(12) United States Patent
Skerra et al.

(10) Patent No.: US 9,637,471 B2
(45) Date of Patent: May 2, 2017

(54) HYDROXYINDALPINE DERIVATIVES AND THEIR MEDICAL USE

(71) Applicant: Technische Universitat Munchen, Munich (DE)

(72) Inventors: Arne Skerra, Freising (DE); Michael Muller, Olching (DE); Michael Schemann, Kranzberg (DE); Thomas Berger, Munich (DE)

(73) Assignee: Technische Universitat Munchen, Munich (DE)

( * ) Notice: Subject to any disclaimer, the term of this patent is extended or adjusted under 35 U.S.C. 154(b) by 0 days.

(21) Appl. No.: 14/768,037

(22) PCT Filed: Feb. 14, 2014

(86) PCT No.: PCT/EP2014/052946
§ 371 (c)(1),
(2) Date: Aug. 14, 2015

(87) PCT Pub. No.: WO2014/125084
PCT Pub. Date: Aug. 21, 2014

(65) Prior Publication Data
US 2015/0376164 A1 Dec. 31, 2015

(30) Foreign Application Priority Data
Feb. 14, 2013 (EP) .................................... 13155252

(51) Int. Cl.
*C07D 401/06* (2006.01)
*A61K 31/454* (2006.01)
*A61K 45/06* (2006.01)

(52) U.S. Cl.
CPC .......... *C07D 401/06* (2013.01); *A61K 31/454* (2013.01); *A61K 45/06* (2013.01)

(58) Field of Classification Search
CPC .................................................. C07D 401/06
USPC ......................................... 514/323; 546/201
See application file for complete search history.

(56) References Cited

U.S. PATENT DOCUMENTS 4,064,255 A  12/1977 Champseix

FOREIGN PATENT DOCUMENTS

DE         2618152         6/1977

OTHER PUBLICATIONS

Friderichs et al. "Serotonin der . . . " CA83:28056 (1975).*
Branchek et al. "Characterization . . . " J. Neurosci. 8(7) 2582-2595 (1988).*
Ferriz et al. "Prodrug design . . . " Current Pharm. Design 16 p. 2033-2052 (2010).*
Gueremy et al. "3-(piperidinylalkyl . . . " J. Med. Chem. 23 p. 1306-1310 (1980).*
Pavan et al. "Progress in drug delivery . . . " Molecules 13, 1035-65 (2008).*
Perez et al. "Evaluating prodrug . . . " ChemMedChem 8(10)1662-7 (2013).*
Springer et al. "Optimization of alkylation . . . " J. Med. Chem. 39 p. 5051-5065 (1995).*
Glennon et al. "Serotonin receptor . . . " p. 1-18 (2000).*
Rao et al. "The bowel . . . " Nar. Rev. p. 517-527 (2016).*
Prodrug definition, p. 1,from Am. Heritage dictionary (2013).*
Beattie D.T. et al., "Serotonin Pharmacology in the Gastrointestinal Tract: A Review", *Naunyn Schmiedebergs Arch Pharamacol.* ,2008, 377(3):181-203.
Branchek T. et al., "Enteric Receptors for 5-Hydroxytryptamine*", *Brain Res.*, 1984, 324(1):107-18.
Branchek T.A. et al., Characterization and Localization of a Peripheral Neural 5-Hydroxytryptamine Receptor Subtype (5-HT$_{1P}$) With a Selective Agonist, $^3$H-5-Hydroxyindalphine, *J. Neuroscience*, 1988, 8:2582-95.
Coleman, R.S. et al., "Chemoselective Cleavage of Benzyl Ethers, Esters, and Carbamates in the Presence of Other Easily Reducible Groups", *Synthesis*, 1999, SI:1399-400.
Database Registry [Online] Chemical Abstracts Service, Columbus, Ohio, U.S. May 4, 1986, XP002696170, Database Accession No. 101832-89-7, Compound with Registry No. 101832-89-7.
Foxx-Orenstein AE et al., "Distinct 5-HT Receptors Mediate the Peristaltic Reflex Induced by Mucosal Stimuli in Human and Guinea Pig Intestine", *Gastroenterology*, 1996, 111(5):1281-90.
Friderichs E., "Uber Serotonindervate mit Cyclisierter Seitenkette, 1 Mitt. Darstellung der isomeren 3-(Pyridylmethyl)-und 3-(Piperidylmethyl)-5-h ydrox yindole", *Arch. Pharmaz*, vol. 308, No. 3, 1975, pp. 209-217.

(Continued)

*Primary Examiner* — Celia Chang
(74) *Attorney, Agent, or Firm* — Mueting, Raasch & Gebhardt, P.A.

(57) ABSTRACT

The present invention relates to hydroxyindalpine derivatives of formula (I) as defined herein and pharmaceutical compositions comprising these compounds, as well as their medical use, particularly in the treatment or prevention of gastrointestinal diseases/disorders, such as constipation and functional dyspepsia.

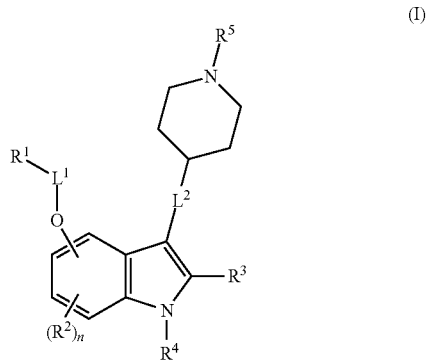

16 Claims, 7 Drawing Sheets

(56) References Cited

OTHER PUBLICATIONS

Figure 1:
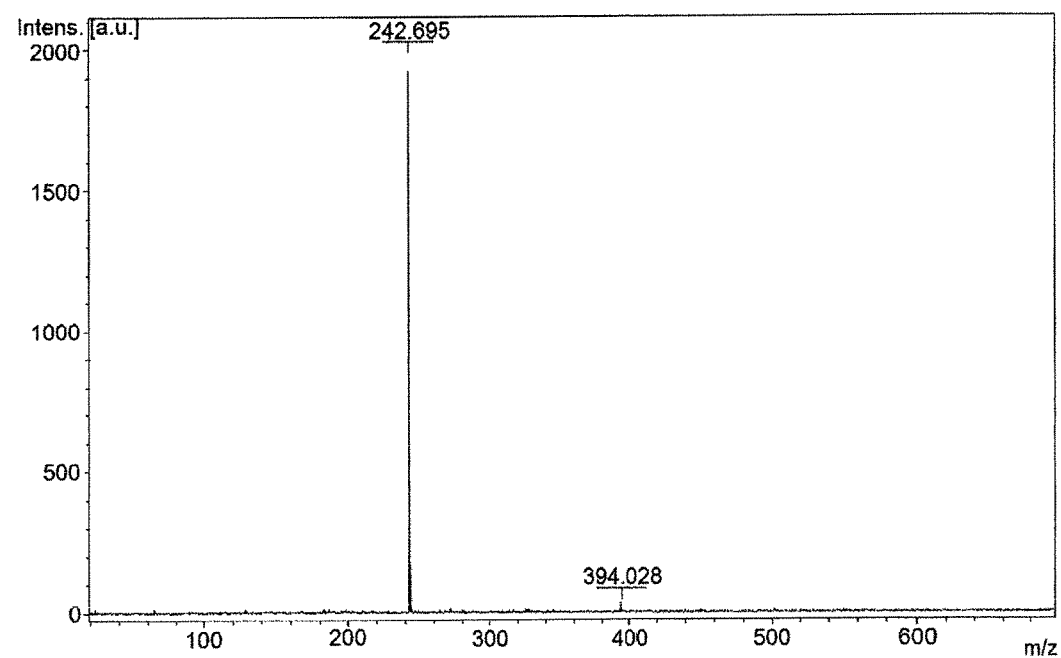

Gershon M.D. et al., "The Enteric Neural Receptor for 5-Hydroxytryptamine", *Experientia*, 1985; 41(7) 863-8.

Gueremy C. et al., "3-(4-Piperidinylalkyl)indoles, Selective Inhibitors of Neuronal 5-Hydroxytryptamine Uptake", *J. Med Chem*, 1980, 23(12):1306-10.

Hutchins R.O. et al., Reduction of C=X to $CH_2$ by Wolff-Kishner and Other Hydrazone Methods, *Comprehensive Organic Synthesis*, 1991, 8:327-43.

International Search Report and Written Opinion for PCT/EP2014/052946 dated Mar. 31, 2014 (9 pages).

Ketcha D.M. et al., "A Convenient Synthesis of 3-Acylindoles via Friedel-Crafts Acylation of 1-(Phenylsufonlyl)indole. A New Route to Pyridocarbazole-5,11-quinones and Ellipticine", *J. Org Chem*, 1989, 54(18):4350-56.

Ketcha D.M., et al., "Synthesis of Alkyl-Substituted N-Protected Indoles via Acylation and Reductive Deoxygenation", *J. Org. Chem*, 1985, 50(26):5451-57.

Leete E. et al., "The Hydrogenolysis of 3-Hydroxymethylindole and Other Indole Derivatives with Lithium Aluminum Hydride", *Canad J Chem*, 1953, 31:775-84.

Lunn G. et al., "Facile Reduction of Pyridines with Nickel-Aluminum Alloy", *J. Org Chem*, 1986, 51:513-17.

Mandal P.K. et al., "Pd-C-Induced Catalytic Transfer Hydrogenation with Triethylsilane", *J Org Chem*, 2007, 72:6599-601.

Mawe G.M. et al., "Peripheral Neural Serotonin Receptors" Identification and Charaterization with Specific Antagonists and Agonists, *Proc. Natl Acad Sci USA*, 1986; 83(24) 9799-803.

Michel K. et al., "Subpopulations of Gastric Myenteric Neurons Are Differentially Activated via Distinct Serotonin Receptors: Projection, Neurochemical Coding, and Functional Implications", *J. Neurosci*. 1997. 17(20) 8009-17.

Mitchell NA et al, "5-Hydroxyindalphine, an Agonist at the Putative 5-$HT_{1P}$ Receptor, Has no Activity on Human Recombinant Monoamine Receptors but Accelerates Distension-Inducated Peristalsis in Mouse Isolated Colon", *Neurogastroenterol Montil*. 2009, 21(7):760-e48).

Szmant, H.H., "The Mechanism of the Wolff-Kishner Reduction, Elimination, and Isomerization Reactions", *Angew Chem Int. Ed.* 1968, 7:120-8.

Takaki M. et al., "Specific Antogonism of Enteric Neural Serotonin Receptors by Dipeptides of 5-Hydroxtryptophan: Evidence that Serotonin is a Medicator of Slow Synaptic Excitation in the Myenteric Plexus[1]", *J. Neurosci*. 1985, 5(7):1769-80.

Wouters, M.M. et al., 5-HT Receptors on Interstitial Cells of Cajal, Smooth Muscle and Enteric Nerves, *Neurogastroenterol Montil.*, 2007, 19 Suppl 2:5-12.

\* cited by examiner

HYDROXYINDALPINE DERIVATIVES AND THEIR MEDICAL USE

The present application is a U.S. National Stage Application of International Application No. PCT/EP2014/052946, filed on Feb. 14, 2014, which was published in English on Aug. 21, 2014, as International Patent Publication WO 2014/125084 A1. International Application No. PCT/EP2014/052946 claims priority to European Application No. 13155252.3 filed Feb. 14, 2013.

The present invention relates to hydroxyindalpine derivatives of formula (I) as defined herein and pharmaceutical compositions comprising these compounds, as well as their medical use, particularly in the treatment or prevention of gastrointestinal diseases/disorders, such as constipation and functional dyspepsia.

Gastrointestinal (GI) disorders can be caused by disturbances of the transit in the gastrointestinal tract and can lead to serious health issues. Constipation, for example, is the most common digestive complaint in the USA, particularly among women and elderly people, and can cause painful defecation. Functional dyspepsia, irritable bowel syndrome, intestinal pseudo-obstruction and other gastrointestinal disorders associated with impaired gastrointestinal motility likewise affect human and animal health.

Gut movements in the gastrointestinal tract are based on the peristaltic reflex which is controlled by the enteric nervous system (ENS) located within the gut wall. ENS sensors detect the stretching of the gut wall and initiate muscle contractions proximal to the stimulus and relaxations distal to the stimulus, resulting in a peristaltic wave that propagates and propels contents through the digestive tract. Gut movements are regulated by serotonin (i.e., 5-hydroxytryptamine or 5-HT) which is released from enterochromaffin cells in the epithelium lining the lumen of the gut and by nerves. The effects of 5-HT are mediated by different receptors, some of which are expressed on various gastrointestinal cell types including enteric nerve cells of the ENS, smooth muscle cells and interstitial cells of Cajal. In particular, 5-$HT_1$, 5-$HT_2$, 5-$HT_3$, 5-$HT_4$ and 5-$HT_7$ receptors are expressed in the gastrointestinal tract and affect gastrointestinal motor function (Wouters M M, et al. *Neurogastroenterol Motil.* 2007; 19 Suppl 2:5-12).

A particularly important receptor in the gut is the putative peripheral 5-$HT_{1P}$ receptor which has been defined pharmacologically and classified as belonging to the 5-$HT_1$ receptor subfamily based on its high affinity for 5-HT (Branchek T, et al. *Brain Res.* 1984; 324(1):107-18; Gershon M D, et al. *Experientia.* 1985; 41(7):863-8). 5-$HT_{1P}$ receptor stimulation results in an activation of enteric nerve cells (Mawe G M, et al. *Proc Natl Acad Sci USA.* 1986; 83(24):9799-803; Michel K, et al. *J Neurosci.* 1997; 17(20):8009-17). The inhibition of the 5-$HT_{1P}$ receptor interferes with the peristaltic reflex and, conversely, the activation of the 5-$HT_{1P}$ receptor initiates peristalsis and thus improves gut transit (Foxx-Orenstein A E, et al. *Gastroenterology.* 1996; 111(5): 1281-90). In the stomach, the activation of the 5-$HT_{1P}$ receptor results in a relaxation of gastric smooth muscle cells, which is mediated by the activation of nitrergic enteric nerve cells (Michel K, et al. *J Neurosci.* 1997; 17(20):8009-17). The activation of the 5-$HT_{1P}$ receptor thus improves gastric accommodation. A selective agonist of the 5-$HT_{1P}$ receptor would hence promote the desirable physiological responses of both stomach and intestine to ingestion and would thereby relieve gastrointestinal complaints.

In the literature, 5-hydroxyindalpine (5-OHIP) and 6-hydroxyindalpine (6-OHIP) have been reported to act as agonists of the 5-$HT_{1P}$ receptor (Branchek T, et al. *Brain Res.* 1984; 324(1):107-18). 5-OHIP has been demonstrated to accelerate peristalsis in mouse isolated colon in a concentration dependent manner and to reduce the threshold pressure required to trigger the peristaltic reflex (Mitchell N A, et al. *Neurogastroenterol Motil.* 2009; 21(7):760-e48). 5-Hydroxytryptophan dipeptide (5-HT-DP or 5-HTP-DP), i.e. N-acetyl-5-hydroxytrytophyl-5-hydroxytryptophan amide, has been described as a 5-$HT_{1P}$ receptor antagonist and utilized in studies of 5-$HT_{1P}$ receptor modulation (Takaki M, et al. *J Neurosci.* 1985; 5(7):1769-80). The preparation of 5-OHIP and 6-OHIP from 3-(4-pyridylethyl)-5-(benzyloxy)indole and 3-(4-pyridylethyl)-6-(benzyloxy) indole, respectively, in a single catalytic hydrogenation step has been described in Gueremy C, et al. *J Med Chem.* 1980; 23(12):1306-10. Related compounds are further disclosed in DE-A-2618152. Moreover, the compound 5-(phenylmethoxy)-3-(4-piperidinylmethyl)-1H-indole has been entered in the Chemical Abstracts Services Registry under the number 101832-89-7, and the hydrogen oxalate salt of the compound 3-(N-methyl-4-piperidinylmethyl)-5-benzyloxyindole has been described as a synthetic intermediate in Friderichs E, et al. *Arch Pharm (Weinheim).* 1975; 308(3): 209-17.

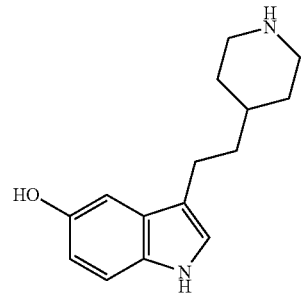

5-Hydroxyindalpine
(5-OHIP)

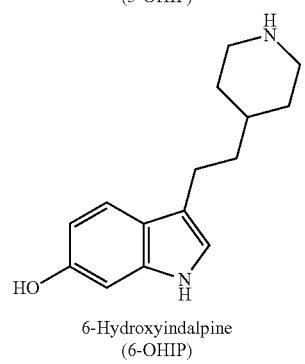

6-Hydroxyindalpine
(6-OHIP)

However, no pharmaceuticals targeting the 5-$HT_{1P}$ receptor have been developed for the treatment of gastrointestinal disorders to date (Beattie D T, et al. *Naunyn Schmiedebergs Arch Pharmacol.* 2008; 377(3):181-203). Unfortunately, the known 5-$HT_{1P}$ receptor agonists 5-OHIP and 6-OHIP are highly susceptible to oxidation and therefore chemically instable, which severely limits their potential use as pharmaceuticals. 5-OHIP and 6-OHIP are not commercially available and are furthermore difficult to synthesize, requiring considerable efforts to obtain even low yields.

It would thus be desirable to provide novel agonists of the 5-$HT_{1P}$ receptor for the medical intervention of gastrointestinal disorders, which should preferably not suffer from the above-described drawbacks associated with 5-OHIP and 6-OHIP.

In the context of the present Invention, it has been found that the hydroxyindalpine derivatives described herein do not only have an improved chemical stability but, surprisingly, retain agonistic activity on the 5-HT$_{1P}$ receptor, which makes them suitable for the treatment or prevention of gastrointestinal disorders. It is therefore an object of the present invention to provide novel hydroxyindalpine derivatives useful as 5-HT$_{1P}$ receptor agonists for the treatment or prevention of gastrointestinal disorders which are particularly stable, act selectively on the 5-HT$_{1P}$ receptor and can be readily synthesized.

Accordingly, the present invention provides a compound of the following formula (I):

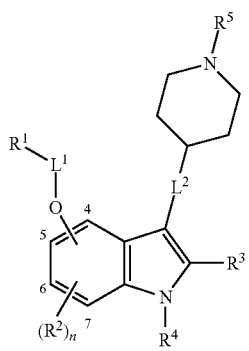

or a pharmaceutically acceptable salt, solvate or prodrug thereof, for use as a medicament, $L^1$ is $C_1$ alkylene, wherein one —CH$_2$— unit comprised in said $C_{1-4}$ alkylene is optionally replaced by —O—, —CO—, —S—, —SO— or —SO$_2$—, preferably by —O— or —S—. It is to be understood that, if $L^1$ is —CH$_2$—, an optional replacement of one —CH$_2$— unit is not possible. If one —CH$_2$— unit comprised in the $C_{1-4}$ alkylene is replaced by —O— or —S—, it is preferred that the —CH$_2$— unit to be replaced is not adjacent to the oxygen atom to which $L^1$ is bound. Preferably, $L^1$ is —(CH$_2$)$_{1-4}$—, more preferably $L^1$ is —CH$_2$— or —CH$_2$CH$_2$—, and most preferably $L^1$ is —CH$_2$—.

$L^2$ is $C_{1-4}$ alkylene. Preferably, $L^2$ is —CH$_2$—, —CH$_2$CH$_2$— or —CH$_2$CH$_2$CH$_2$—, more preferably $L^2$ is —CH$_2$CH$_2$— or —CH$_2$CH$_2$CH$_2$—, and most preferably $L^2$ is —CH$_2$CH$_2$—.

$R^1$ is aryl or heteroaryl, wherein said aryl or heteroaryl is optionally substituted with one or more (e.g., one, two, three or four; preferably one or two, more preferably one) groups independently selected from $C_{1-4}$ alkyl (e.g., methyl or ethyl), halogen, —CF$_3$, —CN, —OH, —O($C_{1-4}$ alkyl) (e.g., methoxy or ethoxy), —SH, —S($C_{1-4}$ alkyl), —NH$_2$, —NH($C_{1-4}$ alkyl), or —N($C_{1-4}$ alkyl)($C_{1-4}$ alkyl). It is preferred that said aryl is phenyl or naphthyl; more preferably, said aryl is phenyl. It is preferred that said heteroaryl has 5 or 6 ring atoms, wherein 1, 2 or 3 ring atoms are each independently selected from oxygen, sulfur or nitrogen and the other ring atoms are carbon atoms. For example, said heteroaryl may be selected from pyridinyl, thienyl, furyl, pyrrolyl, imidazolyl, pyrazolyl, pyrazinyl, pyrimidinyl, pyridazinyl, oxazolyl, isoxazolyl, or furazanyl.

Preferably, $R^1$ is phenyl optionally substituted with one or more (e.g., one, two, three or four; preferably one or two, more preferably one) groups independently selected from $C_{1-4}$ alkyl, halogen, —CF$_3$, —CN, —OH, —O($C_{1-4}$ alkyl), —SH, —S($C_{1-4}$ alkyl), —NH$_2$, —NH($C_{1-4}$ alkyl), or —N($C_{1-4}$ alkyl)($C_{1-4}$ alkyl). More preferably, $R^1$ is phenyl (i.e., unsubstituted phenyl).

It is preferred that the moiety —O-$L^1$-$R^1$ is bound to position 5 or 6 of the indole ring of the compound of formula (I), more preferably to position 5 of the indole ring.

Each $R^2$ is independently selected from $C_{1-4}$ alkyl (e.g., methyl or ethyl), halogen, —CF$_3$, —CN, —OH, —O($C_{1-4}$ alkyl) (e.g., methoxy or ethoxy), —SH, —S($C_{1-4}$ alkyl), —NH$_2$, —NH($C_{1-4}$ alkyl), or —N($C_{1-4}$ alkyl)($C_{1-4}$ alkyl). Preferably, each $R^2$ is independently selected from $C_{1-4}$ alkyl, halogen, —CF$_3$, —CN, —OH, —O($C_{1-4}$ alkyl), —NH$_2$, —NH($C_{1-4}$ alkyl), or —N($C_{1-4}$ alkyl)($C_{1-4}$ alkyl).

$R^3$ is selected from hydrogen, $C_{1-4}$ alkyl (e.g., methyl or ethyl), halogen, —CF$_3$, —CN, —OH, —O($C_{1-4}$ alkyl) (e.g., methoxy or ethoxy), —SH, —S($C_{1-4}$ alkyl), —NH$_2$, —NH($C_{1-4}$ alkyl), or —N($C_{1-4}$ alkyl)($C_{1-4}$ alkyl). Preferably, $R^3$ is hydrogen.

$R^4$ is selected from hydrogen, $C_{1-4}$ alkyl (e.g., methyl or ethyl), or —CO($C_{1-4}$ alkyl) (e.g., formyl or acetyl). Preferably, $R^4$ is hydrogen or $C_{1-4}$ alkyl. More preferably, $R^4$ is hydrogen.

$R^5$ is selected from hydrogen, $C_{1-4}$ alkyl (e.g., methyl or ethyl), or —CO($C_{1-4}$ alkyl) (e.g., formyl or acetyl). Preferably, $R^5$ is hydrogen or $C_{1-4}$ alkyl. More preferably, $R^5$ is hydrogen.

n is 0, 1, 2 or 3. Preferably, n is 0 or 1. More preferably, n is 0.

It is to be understood that, if n is 0, there are no substituents $R^2$ on the indole moiety of the compound of formula (I), i.e. the corresponding indole ring atoms are bound to hydrogen.

It is particularly preferred that the compound of formula (I) is a compound of the following formula (II) or a pharmaceutically acceptable salt, solvate or prodrug thereof:

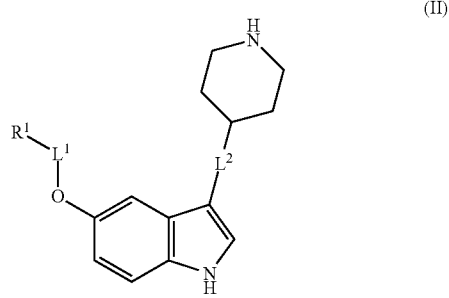

$L^1$ is —(CH$_2$)$_{1-4}$—. Preferably, $L^1$ is —CH$_2$— or —CH$_2$CH$_2$—, and more preferably $L^1$ is —CH$_2$—.

$L^2$ is —CH$_2$—, —CH$_2$CH$_2$— or —CH$_2$CH$_2$CH$_2$—. Preferably, $L^2$ is —CH$_2$CH$_2$— or —CH$_2$CH$_2$CH$_2$—, and more preferably $L^2$ is —CH$_2$CH$_2$—.

$R^1$ is phenyl optionally substituted with one or more (e.g., one, two, three or four; preferably one or two, more preferably one) groups independently selected from $C_{1-4}$ alkyl, halogen, —CF$_3$, —CN, —OH, —O($C_{1-4}$ alkyl), —SH, —S($C_{1-4}$ alkyl), —NH$_2$, —NH($C_{1-4}$ alkyl), or —N($C_{1-4}$ alkyl)($C_1$ alkyl). Preferably, $R^1$ is phenyl (i.e., unsubstituted phenyl).

A particularly preferred compound of formula (I) is 5-benzyloxyindalpine (5-BOIP) having the following structure:

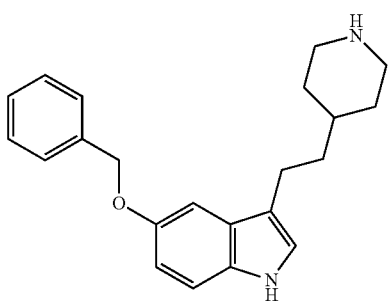 [SMILES: c1ccc(COc2ccc3[nH]cc(CCC4CCNCC4)c3c2)cc1]

or a pharmaceutically acceptable salt, solvate or prodrug thereof.

A further particularly preferred compound of formula (I) is homo-5-benzyloxyindalpine (homo-5-BOIP) having the following structure:

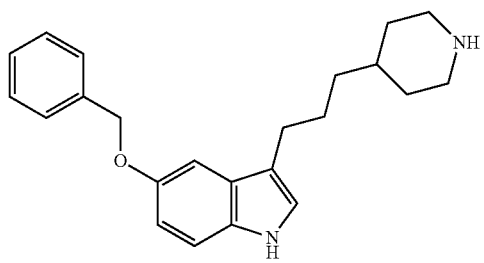 [SMILES: c1ccc(COc2ccc3[nH]cc(CCCC4CCNCC4)c3c2)cc1]

or a pharmaceutically acceptable salt, solvate or prodrug thereof,

A further preferred compound of formula (I) is 6-benzyloxyindalpine (6-BOIP) shown in the following:

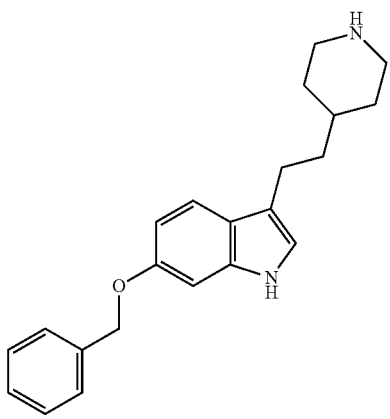 [SMILES: c1ccc(COc2ccc3c(CCC4CCNCC4)c[nH]c3c2)cc1]

or a pharmaceutically acceptable salt, solvate or prodrug thereof.

A further preferred compound of formula (I) is homo-6-benzyloxyindalpine (homo-6-BOIP) shown in the following:

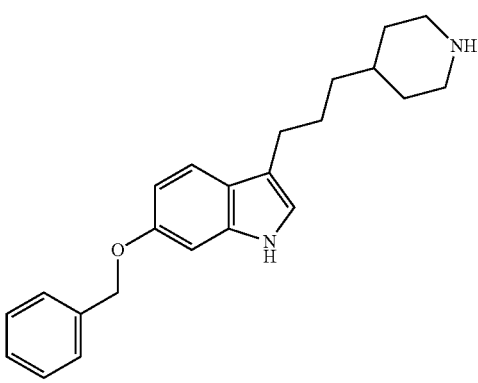 [SMILES: c1ccc(COc2ccc3c(CCCC4CCNCC4)c[nH]c3c2)cc1]

or a pharmaceutically acceptable salt, solvate or prodrug thereof.

The present invention furthermore provides novel compounds characterized by the following formula (I-1):

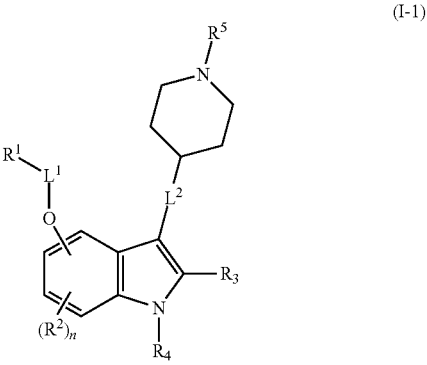

(I-1)

or a pharmaceutically acceptable salt, solvate or prodrug thereof, wherein $L^1$, $R^1$, $R^2$, $R^3$, $R^4$, $R^5$ and n have the meanings and preferred meanings as described herein above for the compound of formula (I), and further wherein $L^2$ is $C_{2-4}$ alkylene. Preferably, $L^2$ is —CH$_2$CH$_2$— or —CH$_2$CH$_2$CH$_2$—, and more preferably $L^2$ is —CH$_2$CH$_2$—.

The novel compounds provided in the context of the present invention are useful as pharmaceuticals, particularly for the treatment or prevention of a gastrointestinal disease or disorder, as explained further below.

The invention also relates to novel compounds of formula (II-1):

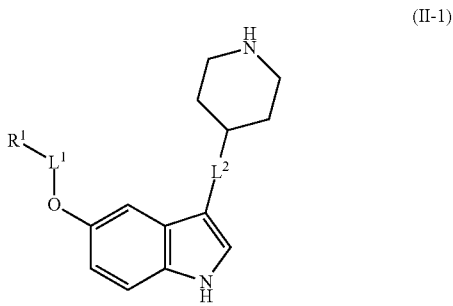

(II-1)

or a pharmaceutically acceptable salt, solvate or prodrug thereof, wherein $L^1$ and $R^1$ have the meanings and preferred meanings as described herein above for the compound of formula (II), and further wherein L² is —CH₂CH₂— or —CH₂CH₂CH₂—. Preferably, L² is —CH₂CH₂—.

The present invention further provides the following novel compounds as well as pharmaceutically acceptable salts, solvates and prodrugs thereof:

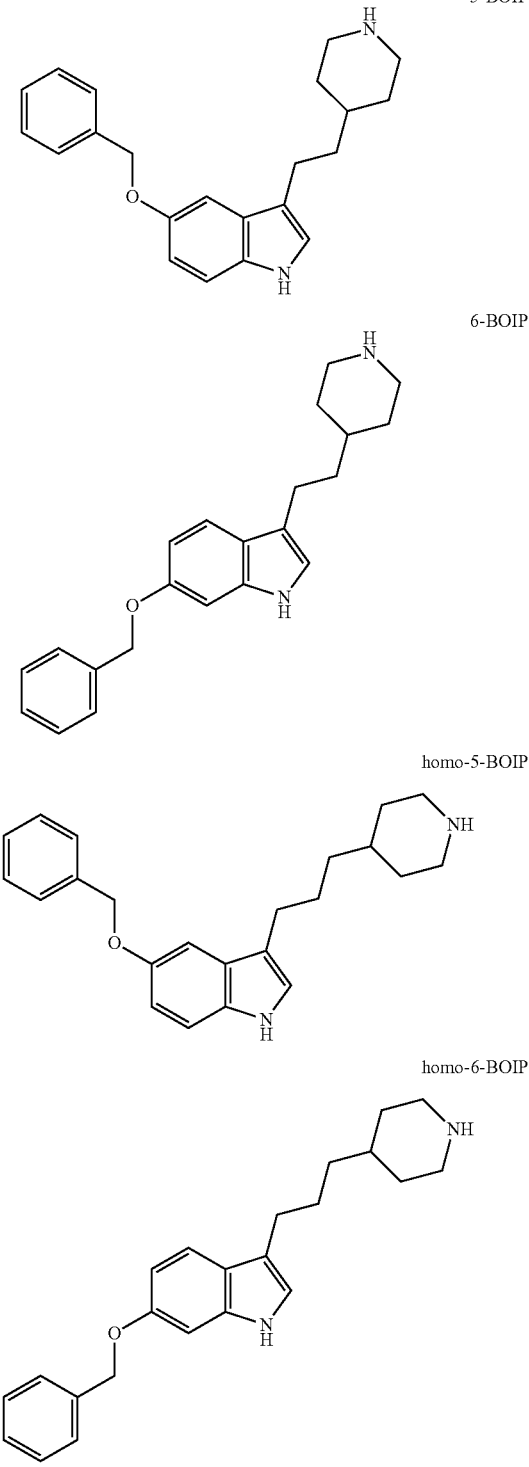

As used herein, the term "alkyl" refers to a monovalent saturated aliphatic (i.e., non-aromatic) acyclic hydrocarbon group (i.e., a group consisting of carbon atoms and hydrogen atoms) which may be linear or branched and does not comprise any carbon-to-carbon double bond or any carbon-to-carbon triple bond. A "$C_{1-4}$ alkyl" denotes an alkyl group having 1 to 4 carbon atoms.

As used herein, the term "alkylene" refers to a divalent saturated aliphatic acyclic hydrocarbon group which may be linear or branched and does not comprise any carbon-to-carbon double bond or any carbon-to-carbon triple bond.

As used herein, the term "aryl" refers to a monovalent aromatic hydrocarbon group, including monocyclic as well as bridged ring and/or fused ring systems, containing at least one aromatic ring. "Aryl" may, for example, refer to phenyl, naphthyl or anthracenyl.

As used herein, the term "heteroaryl" refers to a monovalent aromatic ring group, including monocyclic as well as bridged ring and/or fused ring systems, containing at least one aromatic ring which comprises one or more (such as, e.g., one, two, or three) ring heteroatoms independently selected from O, S, or N. The "heteroaryl" may, e.g., have 5 to 14 ring atoms, particularly 5 or 6 ring atoms. "Heteroaryl" may, for example, refer to thiophenyl (thienyl), furanyl (furyl), pyrrolyl, imidazolyl, pyrazolyl, pyridinyl (pyridyl; including, e.g., 2-pyridyl, 3-pyridyl, and 4-pyridyl), pyrazinyl, pyrimidinyl, pyridazinyl, oxazolyl, isoxazolyl, or furazanyl.

As used herein, the term "halogen" refers to —F, —Cl, —Br or —I, preferably to —F or —Cl.

It has surprisingly been found that compounds of formula (I) exhibit agonistic activity on the 5-HT$_{1P}$ receptor in a neuronal tissue assay. In this connection, it has been demonstrated that 5-benzyloxyindalpine (5-BOIP) activates human enteric nerve cells and that this activation is neutralized by a known 5-HT$_{1P}$ receptor antagonist, 5-HTP-DP, as also reported in Example 4. The agonistic activity of the compounds of formula (I) on the 5-HT$_{1P}$ receptor is particularly surprising as these compounds contain a bulky (hetero)arylalkoxy group in place of the free phenolic hydroxy group which is present in the known 5-HT$_{1P}$ receptor agonists 5-OHIP and 6-OHIP and thus differ markedly from 5-OHIP and 6-OHIP in their capability to undergo hydrogen bonding.

Accordingly, the compounds of the present invention are useful as 5-HT$_{1P}$ receptor agonists and, thus, can be used for the treatment or prevention of gastrointestinal diseases/disorders, particularly gastrointestinal motility diseases/disorders, such as constipation as well as functional dyspepsia and/or associated dyspeptic symptoms. Particularly advantageous are compounds of formula (I) acting selectively on the 5-HT$_{1P}$ receptor. The compounds according to the invention furthermore have an advantageously high stability against oxidation, as discussed further below, which makes them particularly suitable as pharmaceuticals.

Accordingly, the present invention also relates to a pharmaceutical composition comprising a compound of formula (I), or a pharmaceutically acceptable salt, solvate or prodrug thereof, optionally in combination with a pharmaceutically acceptable excipient. The invention thus provides a compound of formula (I), or a pharmaceutically acceptable salt, solvate or prodrug thereof, for use as a medicament.

The invention further relates to a compound of formula (I), or a pharmaceutically acceptable salt, solvate or prodrug thereof, or a pharmaceutical composition comprising any of the aforementioned entities in combination with a pharmaceutically acceptable excipient, for use in the treatment or prevention of a gastrointestinal disease or disorder, in particular a gastrointestinal motility disease or disorder. The present invention likewise relates to the use of a compound of formula (I), or a pharmaceutically acceptable salt, solvate or prodrug thereof, for the preparation of a medicament for treating or preventing a gastrointestinal disease or disorder, in particular a gastrointestinal motility disease or disorder. The invention also provides a compound of formula (I), or a pharmaceutically acceptable salt, solvate or prodrug thereof, or a pharmaceutical composition comprising any of the aforementioned entities in combination with a pharmaceutically acceptable excipient, for use as a prokinetic agent or a prokinetic medicament.

Moreover, the present invention relates to a method of treating or preventing a gastrointestinal disease or disorder, in particular a gastrointestinal motility disease or disorder, the method comprising the administration of a therapeutically effective amount of a compound of formula (I), or a pharmaceutically acceptable salt, solvate or prodrug thereof, or a pharmaceutical composition comprising any of the aforementioned entities optionally in combination with a pharmaceutically acceptable excipient, to a subject in need thereof (preferably a human or a non-human animal, more preferably a human).

The gastrointestinal disease or disorder to be treated or prevented in accordance with the present invention is preferably selected from constipation (including, e.g., acute constipation and chronic constipation, as well as slow transit constipation, idiopathic constipation, constipation due to post-operative ileus, and colonic inertia), dyspepsia (e.g., functional dyspepsia or non-ulcer dyspepsia) and/or associated dyspeptic symptoms, irritable bowel syndrome (e.g., constipation-predominant irritable bowel syndrome or IBS-C), gastroparesis, intestinal pseudo-obstruction (including, e.g., acute intestinal pseudo-obstruction and chronic intestinal pseudo-obstruction), obstructed defecation, abdominal bloating, abdominal distension, fecal impaction, or abdominal pain. The invention particularly relates to the treatment or prevention of constipation as well as the treatment or prevention of functional dyspepsia and/or associated dyspeptic symptoms.

The known 5-HT$_{1P}$ receptor agonists 5-hydroxyindalpine (5-OHIP) and 6-hydroxyindalpine (6-OHIP) are prone to oxidation by oxygen from the air, resulting in the corresponding quinone imine species, as illustrated in the following scheme:

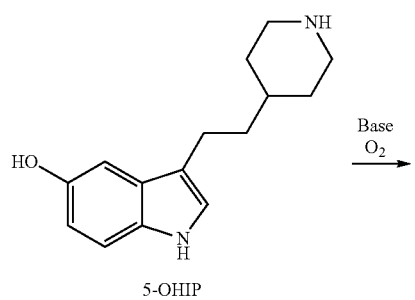

5-OHIP

Base
O$_2$

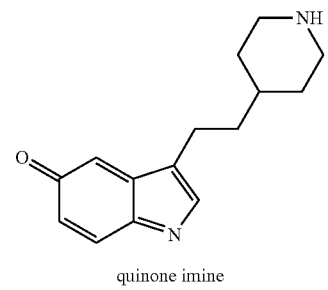

quinone imine

The compounds of the present invention are more stable than 5-OHIP or 6-OHIP, as they do not have a free hydroxy group with an acidic hydrogen atom bound to the indole ring. The formation of oxidized quinone imine species is therefore significantly decreased in the compounds of the present invention, resulting in an advantageously improved chemical stability.

The improved stability of the compounds according to the invention as compared to 5-OHIP or 6-OHIP has been further confirmed by the observation that 5-BOIP retains activity even after storage for 15 months as a solid at 4° C. or in solution frozen at −20° C. while 5-OHIP would lose its activity under the same conditions.

For a person skilled in the field of synthetic chemistry, various ways for the preparation of the compounds of the present invention will be readily apparent. The compounds of formula (I) can, for example, be prepared according to the following general protocol, which is further illustrated in Scheme 1 below. The groups and variables of the compounds shown in Scheme 1, including R$^1$, R$^2$, R$^3$, R$^4$, R$^5$, L$^1$ and n, have the same meanings or preferred meanings described herein above in connection with the compounds of formula (I).

A hydroxyindole derivative (1), which is commercially available or can be prepared in accordance with synthetic protocols described in the literature, is alkylated with an arylalkyl halide or a heteroarylalkyl halide (2) using cesium carbonate and a crown ether (e.g., 18-crown-6) to provide an arylalkyloxyindole or heteroarylalkyloxyindole derivative (3). The (hetero)arylalkyloxyindole derivative (3) is then coupled in a Grignard reaction with an acid chloride (5) which can be prepared from a 1-Cbz-4-piperidinealkanoic acid (4) using a chlorination reagent, such as thionyl chloride (SOCl$_2$), to provide compound (6). The carboxybenzyl (Cbz) protecting group of compound (6) is removed (e.g., by treatment with concentrated HCl) to obtain compound (7). Optionally, compound (7) can further be N-alkylated or N-acylated on its piperidine moiety using, e.g., an alkyl halide or an acyl halide. The carbonyl group in compound (7) is transformed into a methylene group in a Wolff-Kishner reduction using hydrazine (N$_2$H$_4$) and a base (e.g., KOH) to yield the desired compound (8) of formula (I) according to the invention. The reaction conditions in each of these steps, including the reaction temperature and duration, solvents, and the molar ratio of the respective reactants, can be suitably selected, e.g., in accordance with the conditions employed in the corresponding reaction steps in Example 1.

Scheme1: Synthesis of the compounds of formula (I), route A.
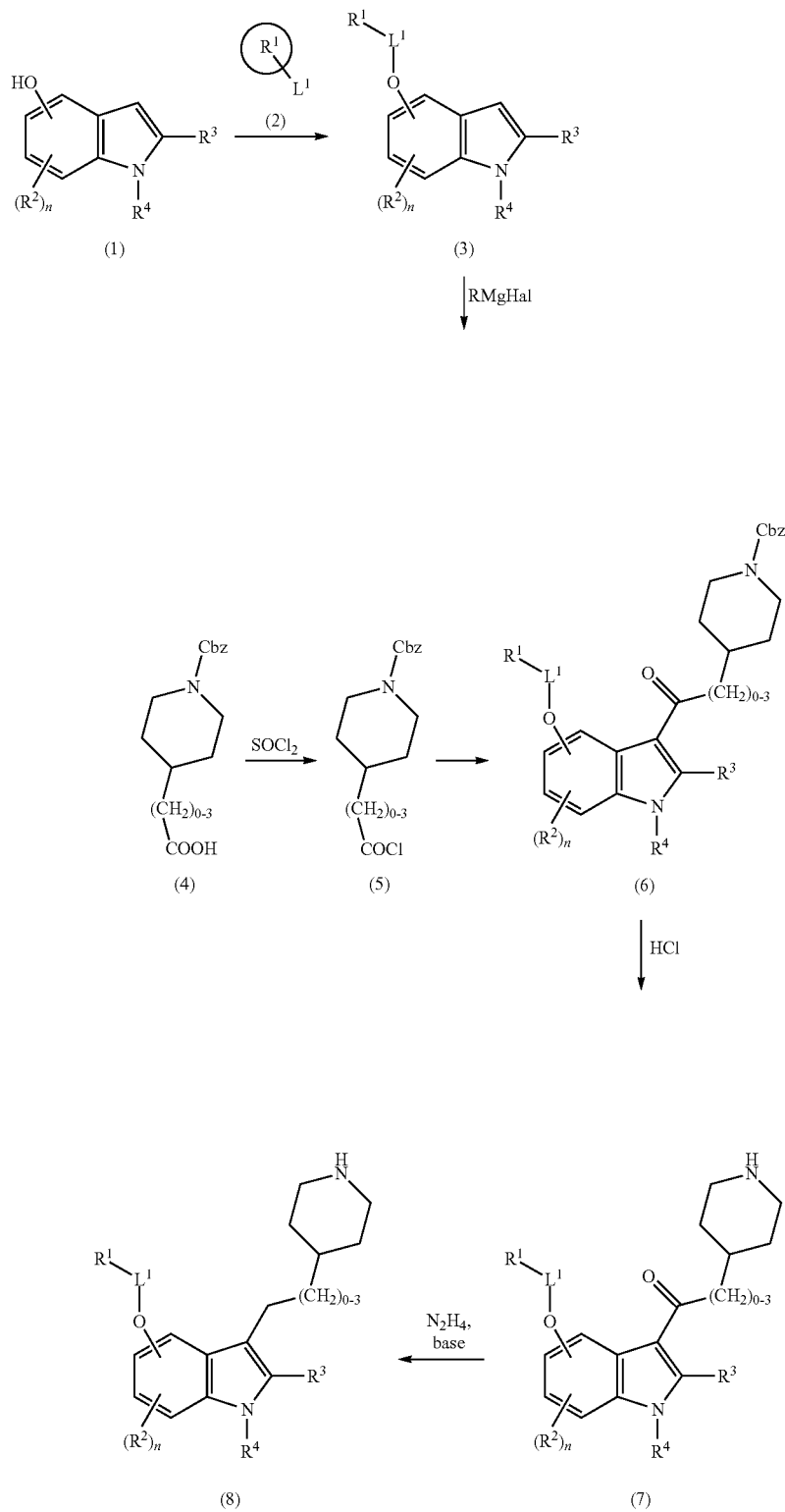

Accordingly, the present invention also relates to a process of preparing the compound of formula (I) or a pharmaceutically acceptable salt, solvate or prodrug thereof, comprising a step of reacting a compound of the following formula (Ia) with hydrazine and a base to obtain the compound of formula (I).

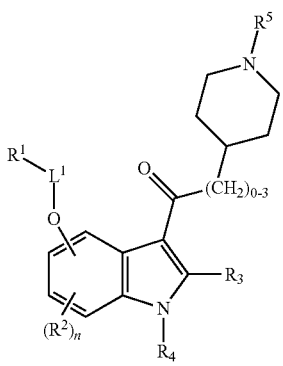

(Ia)

wherein $R^1$, $R^2$, $R^3$, $R^4$, $R^5$, $L^1$ and n in formula (Ia) have the same meanings or preferred meanings as the corresponding groups or variables in the compound of formula (I) as defined and described herein above.

The invention likewise relates to a process of preparing the compound of formula (I-1) or a pharmaceutically acceptable salt, solvate or prodrug thereof, comprising a step of reacting a compound of formula (Ib) with hydrazine and a base to obtain the compound of formula (I-1):

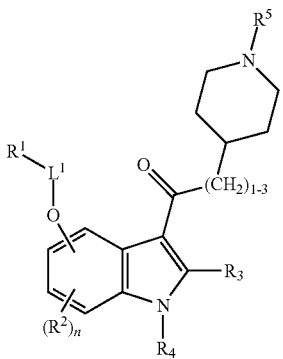

(Ib)

wherein $R^1$, $R^2$, $R^3$, $R^4$, $R^5$, $L^1$ and n in formula (Ib) have the same meanings or preferred meanings as the corresponding groups or variables in the compound of formula (I-1) as described herein above.

The process thus comprises a step of subjecting the compound of formula (Ia) or the compound of formula (Ib) to a Wolff-Kishner reduction by reacting it with hydrazine and a base. The base may, e.g., be an alkali metal hydroxide, such as potassium hydroxide or sodium hydroxide (e.g., solid KOH dissolved in diethylene glycol), or an alkali metal tert-butoxide, such as potassium tert-butoxide or sodium tert-butoxide (e.g, potassium tert-butoxide dissolved in in dimethyl sulfoxide). The reaction conditions in this step can suitably be chosen as described for Wolff-Kishner reductions in the literature (e.g., Hutchins R O, et al. *Comprehensive organic synthesis*. 1991; 8:327-43; or Szmant H H. *Angew Chem Int Ed*. 1968; 7:120-8). In particular, the reaction temperature can be chosen depending on the specific base employed. For example, if potassium hydroxide dissolved in diethylene glycol is used as the base, the reaction may be conducted at a temperature of about 100° C. to about 200° C., preferably at a temperature of about 150° C. The compound of formula (Ia) or the compound of formula (Ib) can be prepared following the synthetic protocol for compound (7) described above and illustrated in Scheme 1. Accordingly, the process of preparing the compound of formula (I) or the compound of formula (I-1) may further comprise the additional reaction steps described in the general synthetic protocol above and illustrated in Scheme 1.

The compounds of formula (I) can also be prepared according to the following alternative protocol, which is further illustrated in Scheme 2 below. The groups and variables of the compounds shown in Scheme 2, including $R^1$, $R^2$, $R^3$, $R^4$, $R^5$, $L^1$ and n, have the same meanings or preferred meanings described herein above in connection with the compounds of formula (I).

A hydroxyindole derivative (1), which is commercially available or can be prepared in accordance with synthetic protocols described in the literature, is alkylated with an arylalkyl halide or a heteroarylalkyl halide (2) using cesium carbonate and a crown ether (e.g., 18-crown-6) to provide an arylalkyloxyindole or heteroarylalkyloxyindole derivative (3). The (hetero)arylalkyloxyindole derivative (3) is then coupled in a Grignard reaction with an acid chloride (5) which can be prepared from a 1-Cbz-4-piperidinealkanoic acid (4b) using a chlorination reagent, such as oxalyl chloride, to provide compound (6). The 1-Cbz-4-piperidinealkanoic acid (4b), in turn, can be prepared from a 4-piperidinealkanoic acid (4a) using benzyloxycarbonyl chloride (Cbz-Cl). The carboxybenzyl (Cbz) protecting group of compound (6) is removed (e.g., by treatment with concentrated HCl) to obtain compound (7). Optionally, compound (7) can further be N-alkylated or N-acylated on its piperidine moiety using, e.g., an alkyl halide or an acyl halide. The carbonyl group in compound (7) is transformed into a methylene group in a reduction using lithium aluminum hydride (LiAlH$_4$) to yield the desired compound (8) of formula (I) according to the invention. The reaction conditions in each of these steps, including the reaction temperature and duration, solvents, and the molar ratio of the respective reactants, can be suitably selected, e.g., in accordance with the conditions employed in the corresponding reaction steps in Example 2 or 3.

Scheme 2: Synthesis of the compounds of formula (I), route B.
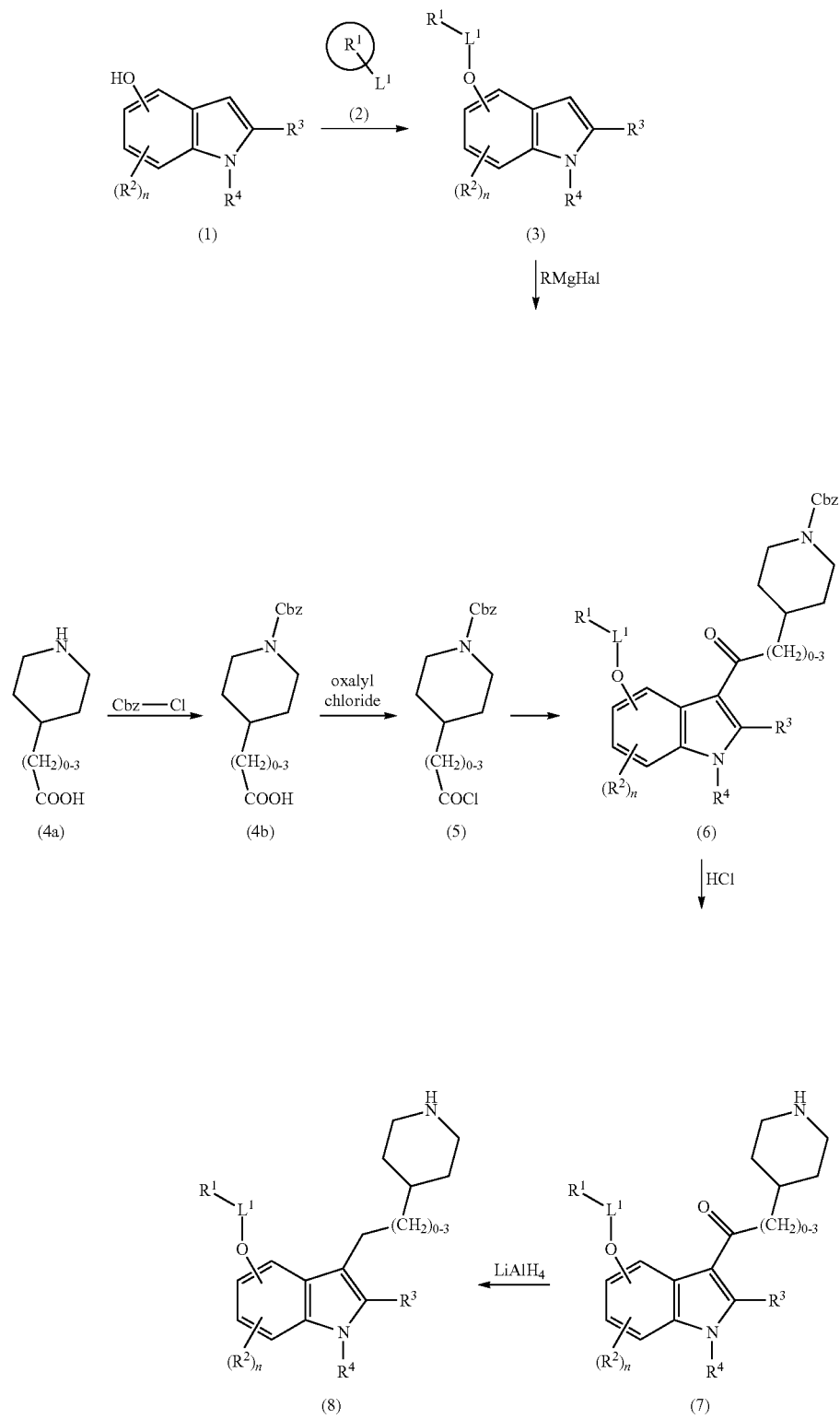

The present invention also relates to a process of preparing the compound of formula (I) or a pharmaceutically acceptable salt, solvate or prodrug thereof, comprising a step of reacting a compound of the following formula (Ia) with lithium aluminum hydride (LiAlH$_4$) to obtain the compound of formula (I):

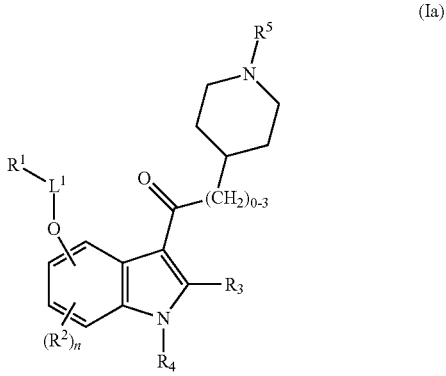

(Ia)

wherein R$^1$, R$^2$, R$^3$, R$^4$, R$^5$, L$^1$ and n in formula (Ia) have the same meanings or preferred meanings as the corresponding groups or variables in the compound of formula (I) as defined and described herein above.

The invention likewise relates to a process of preparing the compound of formula (I-1) or a pharmaceutically acceptable salt, solvate or prodrug thereof, comprising a step of reacting a compound of formula (Ib) with lithium aluminum hydride (LiAlH$_4$) to obtain the compound of formula (I-1):

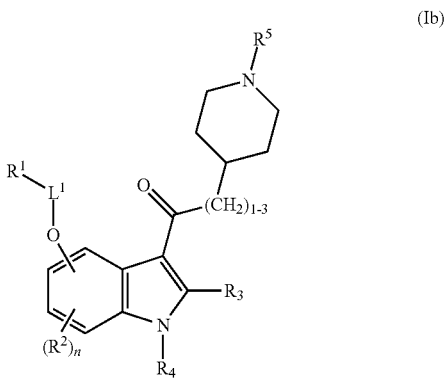

(Ib)

wherein R$^1$, R$^2$, R$^3$, R$^4$, R$^5$, L$^1$ and n in formula (Ib) have the same meanings or preferred meanings as the corresponding groups or variables in the compound of formula (I-1) as described herein above.

The process thus comprises a step of reducing the compound of formula (Ia) or the compound of formula (Ib) by reacting it with lithium aluminum hydride (LiAlH$_4$). The reaction conditions in this step can suitably be chosen as described, e.g., in step (5) of Example 2. The compound of formula (Ia) or the compound of formula (Ib) can be prepared following the synthetic protocol for compound (7) described above and illustrated in Scheme 2. Accordingly, the process of preparing the compound of formula (I) or the compound of formula (I-1) may further comprise the additional reaction steps described in the general synthetic protocol above and illustrated in Scheme 2.

The hydroxyindalpine derivatives of the present invention are also useful as starting materials for the preparation of the corresponding hydroxyindalpines having a free hydroxy group, such as 5-OHIP and 6-OHIP, in a simplified and convenient manner. In particular, a compound of formula (I) can be subjected to hydrogenolysis (e.g., palladium-catalyzed hydrogenolysis) in order to obtain the corresponding hydroxyindalpine having a free hydroxy group. The present invention thereby provides an improved route of synthesis for these hydroxyindalpines. The compounds 5-BOIP and 6-BOIP, for example, can be subjected to hydrogenolysis in order to cleave the benzyl group comprised in these compounds and thereby provide the corresponding hydroxyindalpines 5-OHIP and 6-OHIP, respectively. The hydrogenolysis reaction can, e.g., be carried out using the methods for the cleavage of benzyl ether groups described in: Wuts, P G M and Greene, T W. Greene's Protective Groups in Organic Synthesis, John Wiley & Sons, 4th Edition, 2006; Mandal, P K et al., *J Org Chem*, 2007, 72:6599-601; or Coleman, R S et al., *Synthesis*, 1999, SI:1399-400. Accordingly, the present invention also relates to a method of preparing a hydroxyindalpine having a free hydroxy group, comprising a step of subjecting a compound of formula (I) to hydrogenolysis.

The scope of the present invention embraces all pharmaceutically acceptable salt forms of the compounds of formula (I) which may be formed, e.g., by protonation of an atom carrying an electron lone pair which is susceptible to protonation, such as an amino group, with an inorganic or organic acid, or as a salt of a carboxylic acid group with a physiologically acceptable cation as they are well-known in the art. Exemplary base addition salts comprise, for example: alkali metal salts such as sodium or potassium salts; alkaline earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, or ethylenediamine salts; aralkyl amine salts such as N,N-dibenzylethylenediamine salts, benetamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino add salts such as arginine salts or lysine salts. Exemplary acid addition salts comprise, for example, mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts such as aspartate or glutamate salts.

Moreover, the scope of the invention embraces the compounds of formula (I) in any solvated form, including, e.g., solvates with water, for example hydrates, or with organic solvents such as, e.g., methanol, ethanol or acetonitrile, i.e., as a methanolate, ethanolate or acetonitrilate, respectively, or in the form of any polymorph.

Furthermore, the formulae in the present specification are intended to cover all possible stereoisomers, including enantiomers and diastereomers, of the indicated compounds.

Thus, all stereoisomers of the compounds of the present invention are contemplated as part of the present invention, either in admixture or in pure or substantially pure form. The scope of the compounds according to the invention embraces all of the possible stereoisomers and their mixtures. It particularly embraces the racemic forms and the isolated optical isomers. The racemic forms can be resolved by physical methods, such as, e.g., fractional crystallization, separation or crystallization of diastereomeric derivatives or separation by chiral column chromatography. The individual optical isomers can be obtained from the racemates using conventional methods, such as, e.g., salt formation with an optically active acid followed by crystallization.

Pharmaceutically acceptable prodrugs of the compounds according to the present invention are derivatives which have chemically or metabolically cleavable groups and become, by solvolysis or under physiological conditions, the compounds of the invention which are pharmaceutically active in vivo. Prodrugs of compounds according to the the present invention may be formed in a conventional manner with a functional group of the compounds such as, e.g., with an amino, hydroxy or carboxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). Prodrugs include acid derivatives well known to the person skilled in the art, such as, for example, esters prepared by reaction of the parent acidic compound with a suitable alcohol, or amides prepared by reaction of the parent acid compound with a suitable amine. When a compound of the present invention has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholinoethylester, N,N-diethylglycolamidoester or α-acetoxyethylester. When a compound of the present invention has a hydroxy group, an acyloxy derivative prepared by reacting the hydroxyl group with a suitable acylhalide or a suitable acid anhydride is exemplified as a prodrug. An especially preferred acyloxy derivative as a prodrug is —OC(=O)—CH$_3$, —OC(=O)—C$_2$H$_5$, —OC(=O)-(tert-Bu), —OC(=O)—C$_{15}$H$_{31}$, —OC(=O)-(m-COONa-Ph), —OC(=O)—CH$_2$CH$_2$COONa, —O(C=O)—CH(NH$_2$)CH$_3$ or —OC(=O)—CH$_2$—N(CH$_3$)$_2$. When a compound of the present invention has an amino group, an amide derivative prepared by reacting the amino group with a suitable acid halide or a suitable mixed anhydride is exemplified as a prodrug. An especially preferred amide derivative as a prodrug is —NHC(=O)—(CH$_2$)$_2$OCH$_3$ or —NHC(=O)—CH(NH$_2$)CH$_3$.

The compounds described herein may be administered as compounds per se or may be formulated as medicaments. The medicaments/pharmaceutical compositions may optionally comprise one or more pharmaceutically acceptable excipients, such as carriers, diluents, fillers, disintegrants, lubricating agents, binders, colorants, pigments, stabilizers, preservatives, antioxidants, or solubility enhancers.

In particular, the pharmaceutical compositions may comprise one or more solubility enhancers, such as, e.g., poly(ethylene glycol), including poly(ethylene glycol) having a molecular weight in the range of about 200 to about 5,000 Da, ethylene glycol, propylene glycol, non-ionic surfactants, tyloxapol, polysorbate 80, macrogol-15-hydroxystearate, phospholipids, lecithin, dimyristoyl phosphatidylcholine, dipalmitoyl phosphatidylcholine, distearoyl phosphatidylcholine, cyclodextrins, hydroxyethyl-β-cyclodextrin, hydroxypropyl-β-cyclodextrin, hydroxyethyl-γ-cyclodextrin, hydroxypropyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, carboxyalkyl thioethers, hydroxypropyl methylcellulose, hydroxypropylcellulose, polyvinylpyrrolidone, vinyl acetate copolymers, vinyl pyrrolidone, sodium lauryl sulfate, dioctyl sodium sulfosuccinate, or any combination thereof.

The pharmaceutical compositions can be formulated by techniques known to the person skilled in the art, such as the techniques published in Remington's Pharmaceutical Sciences, 20$^{th}$ Edition. The pharmaceutical compositions can be formulated as dosage forms for oral, parenteral, such as intramuscular, intravenous, subcutaneous, intradermal, intraarterial, intracardial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds according to the invention, or the above described pharmaceutical compositions comprising one or more compounds of formula (I), may be administered to a subject by any convenient route of administration, whether systemically/peripherally or at the site of desired action, including but not limited to one or more of: oral (e.g., as a tablet, capsule, or as an ingestible solution), topical (e.g., transdermal, intranasal, buccal, and sublingual), parenteral (e.g., using injection techniques or infusion techniques, and including, for example, by injection, e.g., subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g., through mouth or nose), gastrointestinal, intrauterine, subcutaneous, rectal, and vaginal.

It is particularly preferred that the compounds or pharmaceutical compositions of the present invention are administered orally, e.g., in the form of tablets, capsules, ovules, elixirs, solutions or suspensions, which may further contain flavoring or coloring agents, for immediate-release, delayed-release, modified-release, sustained-release, pulsed-release or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Alternatively, it may also be possible to administer said compounds or pharmaceutical compositions in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

If said compounds or pharmaceutical compositions are administered parenterally, then examples of such administration include one or more of: intravenously, intraarterially, intraperitoneally, intrathecally, intraventricularly, intraurethrally, intrasternally, intracardially, intracranially, intramuscularly or subcutaneously administering the compounds or pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

For topical application to the skin, said compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compounds according to the invention for oral administration to a human (of approximately 70 kg body weight) may be 0.1 µg to 10 g, preferably 0.1 mg to 1 g, of the active ingredient per unit dose. The unit dose may be administered, for example, 1 to 4 times per day. It will be appreciated that it may be necessary to make routine variations to the dosage depending on the age and weight of the patient/subject as well as the severity of the condition to be treated. The precise dose and also the route of administration will ultimately be at the discretion of the attendant physician or veterinarian.

The compounds of the present invention may be administered in the context of a monotherapy or in combination with one or more other pharmaceutically active agents. When a compound of the invention is used in combination with a second pharmaceutically active agent which is active against the same disease, the dose of each compound may differ from that when the compound is used alone. The combination of a compound of the present invention with one or more other pharmaceutically active agents may comprise the simultaneous/concomitant administration of the pharmaceutically active agents with the compound of the invention. However, sequential/separate administration is also envisaged.

Preferably, the second pharmaceutically active agent to be administered in combination with the compound of the present invention is an agent for the treatment or prevention of a gastrointestinal disease or disorder, such as, e.g., oxyphencyclimine, camylofin, mebeverine, trimebutine, rociverine, dicycloverine, dihexyverine, difemerine, piperidolate, benzilone, glycopyrronium, oxyphenonium, penthienate, propantheline, otilonium bromide, methantheline, tridihexethyl, isopropamide, hexocyclium, poldine, mepenzolate, bevonium, pipenzolate, diphemanil, tiemonium iodide, prifinium bromide, timepidium bromide, fenpiverinium, oxyphenonium, benzetimide, carbachol, neostigmin, dimethylaminopropionylphenothiazine, nicofetamide, tiropramide, papaverine, drotaverine, moxaverine, alosetron, tegaserod, cilansetron, prucalopride, fenpiprane, diisopromine, chlorbenzoxamine, pinaverium, fenoverine, idanpramine, proxazole, alverine, trepibutone, isometheptene, caroverine, phloroglucinol, alverine, physiostigmin, atropine, hyoscyamine, butylscopolamine, methylatropine, methylscopolamine, fentonium, cimetropium bromide, metoclopramide, cisapride, domperidone, bromopride, alizapride, clebopride, physiostigmine, mosapride, zacopride, renzapride, BIMU1, BIMU8, lirexapride, GR125487, cinitapride, itopride, bethanechol, erythromycin, or mitemcinal.

It is particularly preferred that the second pharmaceutically active agent to be administered in combination with the compound of the invention is a 5-HT$_4$ agonist (such as, e.g., tegaserod, mosapride, zacopride, cisapride, renzapride, prucalopride, BIMU1, BIMU8, lirexapride, GR125487, cinitapride, or metoclopramide) or any other prokinetic agent (such as, e.g., itopride, octreotide, bethanechol, domperidone, erythromycin, or mitemcinal).

The combinations referred to above may conveniently be presented for use in the form of a pharmaceutical formulation. The individual components of such combinations may be administered either sequentially or simultaneously/concomitantly in separate or combined pharmaceutical formulations by any convenient route. When administration is sequential, either the compound of the present invention or the second pharmaceutically active agent may be administered first. When administration is simultaneous, the combination may be administered either in the same or different pharmaceutical compositions. When combined in the same formulation it will be appreciated that the two compounds must be stable and compatible with each other and the other components of the formulation. When formulated separately they may be provided in any convenient formulation, conveniently in such manner as is known for such compounds in the art.

Accordingly, the present invention relates to a compound of formula (I) or a pharmaceutically acceptable salt, solvate or prodrug thereof, or a pharmaceutical composition comprising any of the aforementioned entities optionally in combination with a pharmaceutically acceptable excipient, for use in the treatment or prevention of a gastrointestinal disease or disorder, in particular a gastrointestinal motility disease or disorder, whereby the compound or the pharmaceutical composition is to be administered in combination with a further pharmaceutically active agent (such as, e.g., tegaserod, mosapride, zacopride, cisapride, renzapride, prucalopride, BIMU1, BIMU8, lirexapride, GR125487, cinitapride, metoclopramide, itopride, octreotide, bethanechol, domperidone, erythromycin, or mitemcinal).

The subject or patient, such as the subject in need of treatment or prevention, may be an animal (e.g., a non-human animal), a vertebrate animal, a mammal, a rodent (e.g., a guinea pig, a hamster, a rat, a mouse), a murine (e.g., a mouse), a canine (e.g., a dog), a feline (e.g., a cat), a porcine (e.g., a pig), an equine (e.g., a horse), a primate, a simian (e.g., a monkey or ape), a monkey (e.g., a marmoset, a baboon), an ape (e.g., a gorilla, chimpanzee, orangutan, gibbon), or a human. The meaning of the terms "animal", "mammal", etc. is well known in the art and can, for example, be deduced from Wehner und Gehring (1995; Thieme Verlag). In the context of this invention, it is also envisaged that animals are to be treated which are economically, agronomically or scientifically important. Scientifically important organisms include, but are not limited to, mice, rats, and rabbits. Non-limiting examples of agronomically important animals are sheep, cattle and pigs, while, for example, cats and dogs may be considered as economically important animals. Preferably, the subject/patient is a mammal; more preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orangutan, a gibbon, a sheep, cattle, or a pig); even more preferably, the subject/patient is a human.

The term "treatment of a disorder or disease" as used herein is well known in the art. "Treatment of a disorder or disease" implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e., diagnose a disorder or disease).

"Treatment of a disorder or disease" may, for example, lead to a halt in the progression of the disorder or disease (e.g., no deterioration of symptoms) or a delay in the progression of the disorder or disease (in case the halt in progression is of a transient nature only). "Treatment of a disorder or disease" may also lead to a partial response (e.g., amelioration of symptoms) or complete response (e.g., disappearance of symptoms) of the subject/patient suffering from the disorder or disease. "Amelioration" of a disorder or disease may, for example, lead to a halt in the progression of the disorder or disease or a delay in the progression of the disorder or disease. Such a partial or complete response may be followed by a relapse. It is to be understood that a subject/patient may experience a broad range of responses to a treatment (e.g., the exemplary responses as described herein above).

Treatment of a disorder or disease may, inter alia, comprise curative treatment (preferably leading to a complete response and eventually to healing of the disorder or disease) and palliative treatment (including symptomatic relief).

Also the term "prevention of a disorder or disease" as used herein is well known in the art. For example, a patient/subject suspected of being prone to suffer from a disorder or disease as defined herein may, in particular, benefit from a prevention of the disorder or disease. The subject/patient may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of compounds of the present invention before any clinical and/or pathological symptoms are diagnosed or determined or can be diagnosed or determined by the attending physician.

In this specification, a number of documents including patent applications and scientific literature are cited. The disclosure of these documents, while not considered relevant for the patentability of this invention, is herewith incorporated by reference in its entirety. More specifically, all referenced documents are incorporated by reference to the same extent as if each Individual document was specifically and individually indicated to be incorporated by reference.

The invention is also illustrated by the following illustrative figures. The appended figures show:

FIG. 1: Mass spectrum of 5-benzyloxyindalpine (MALDI-TOF; matrix: 2,3,4-trihydroxyacetophenone). The x-axis shows the mass-to-charge ratio (m/z), and the y-axis shows signal intensities ("a.u." means arbitrary units).

Figure 2:
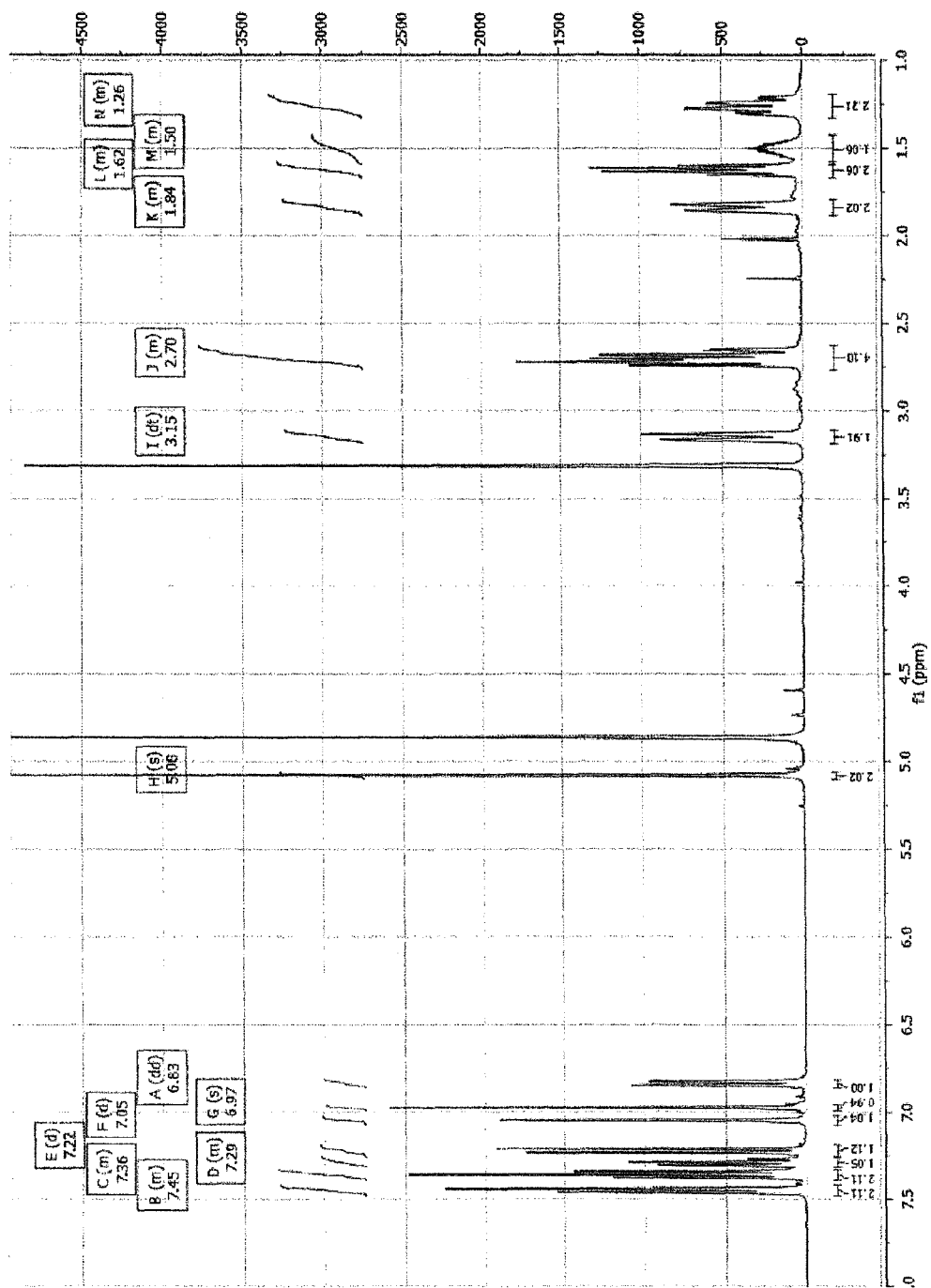

FIG. 2: $^1$H-NMR spectrum of 5-benzyloxyindalpine (5-BOIP); see Example 2.

Figure 3:
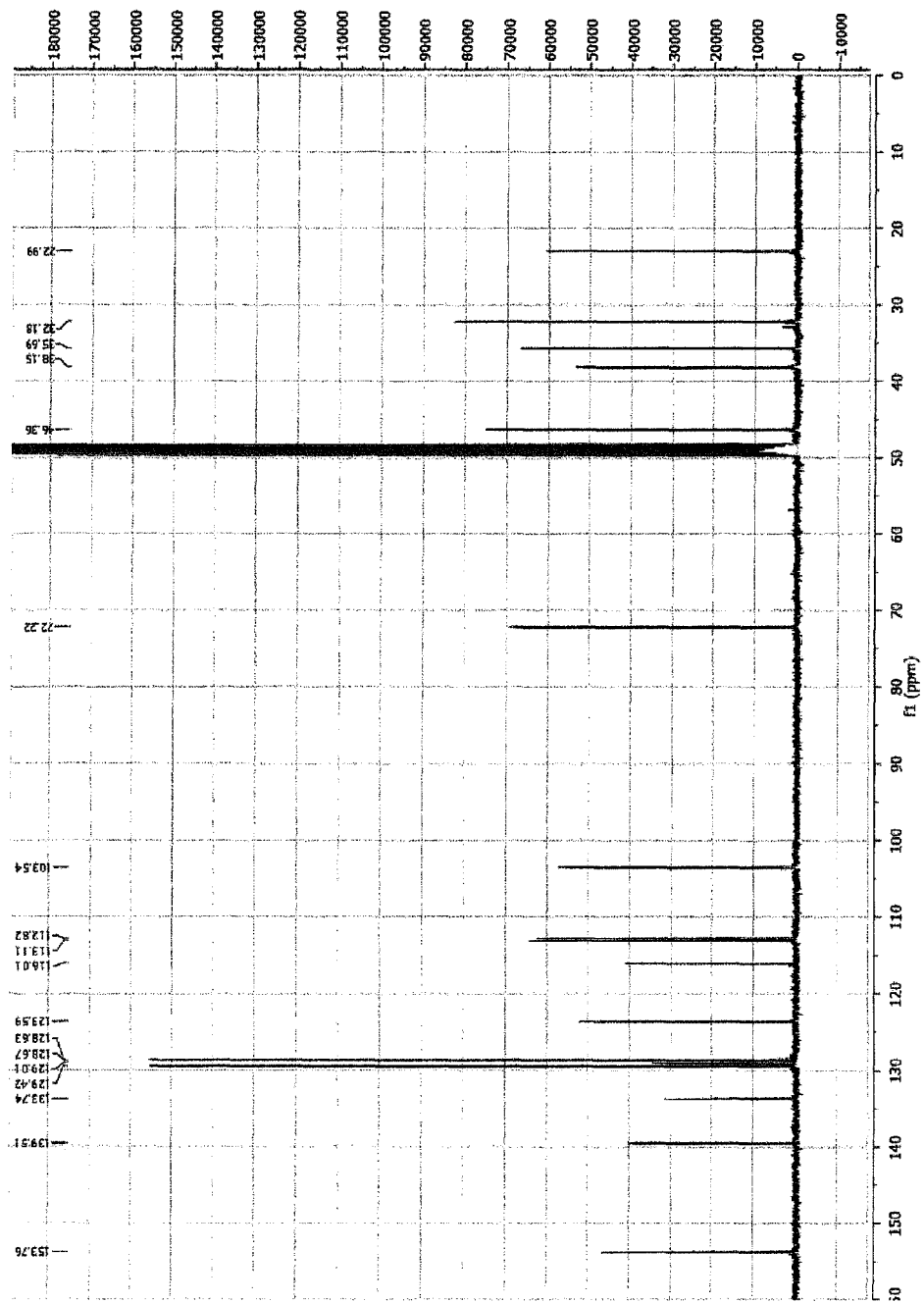

FIG. 3: $^{13}$C-NMR spectrum of 5-benzyloxyindalpine (5-BOIP); see Example 2.

Figure 4:
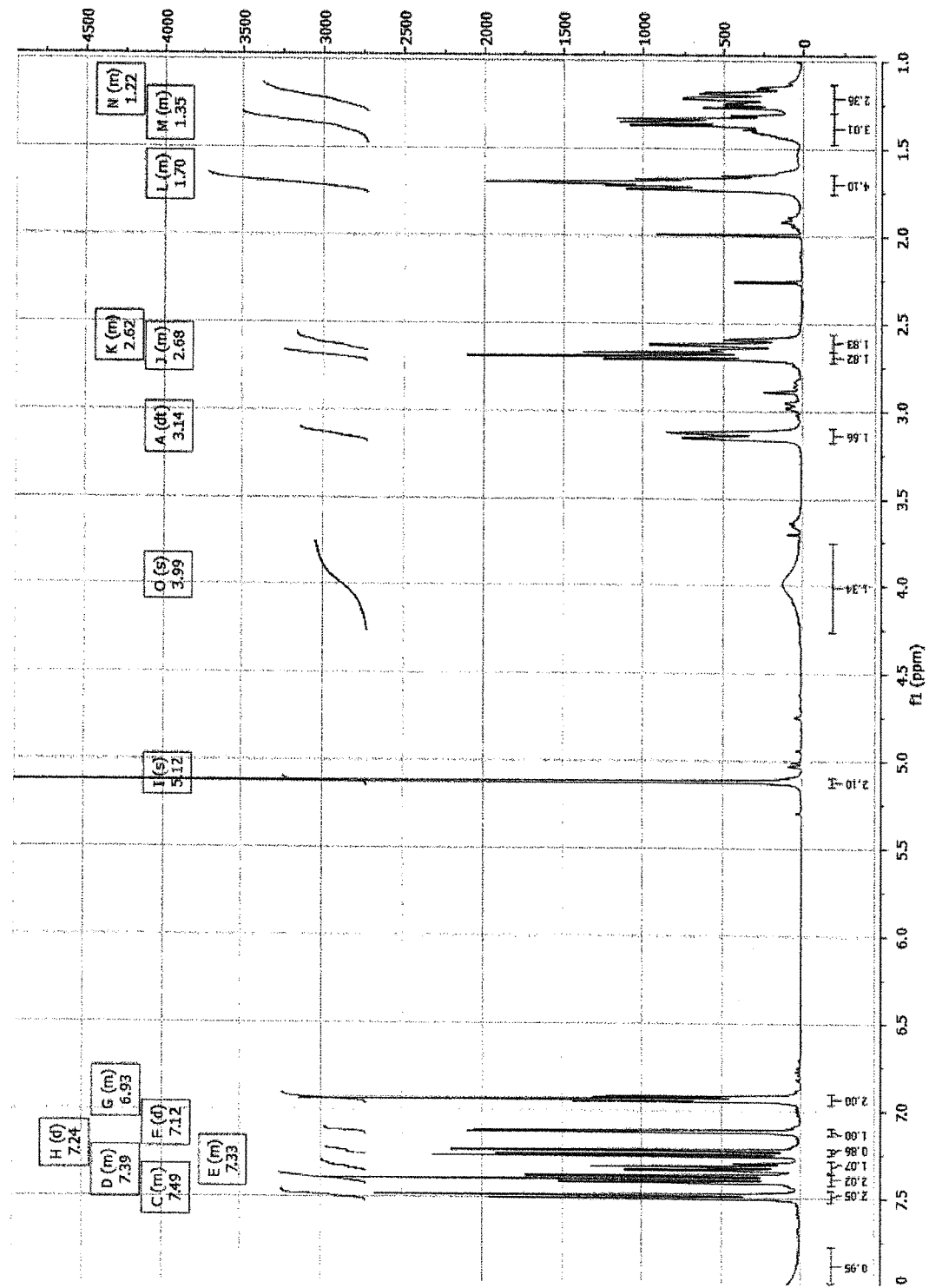

FIG. 4: $^1$H-NMR spectrum of homo-5-benzyloxyindalpine (homo-5-BOIP); see Example 3.

Figure 5:
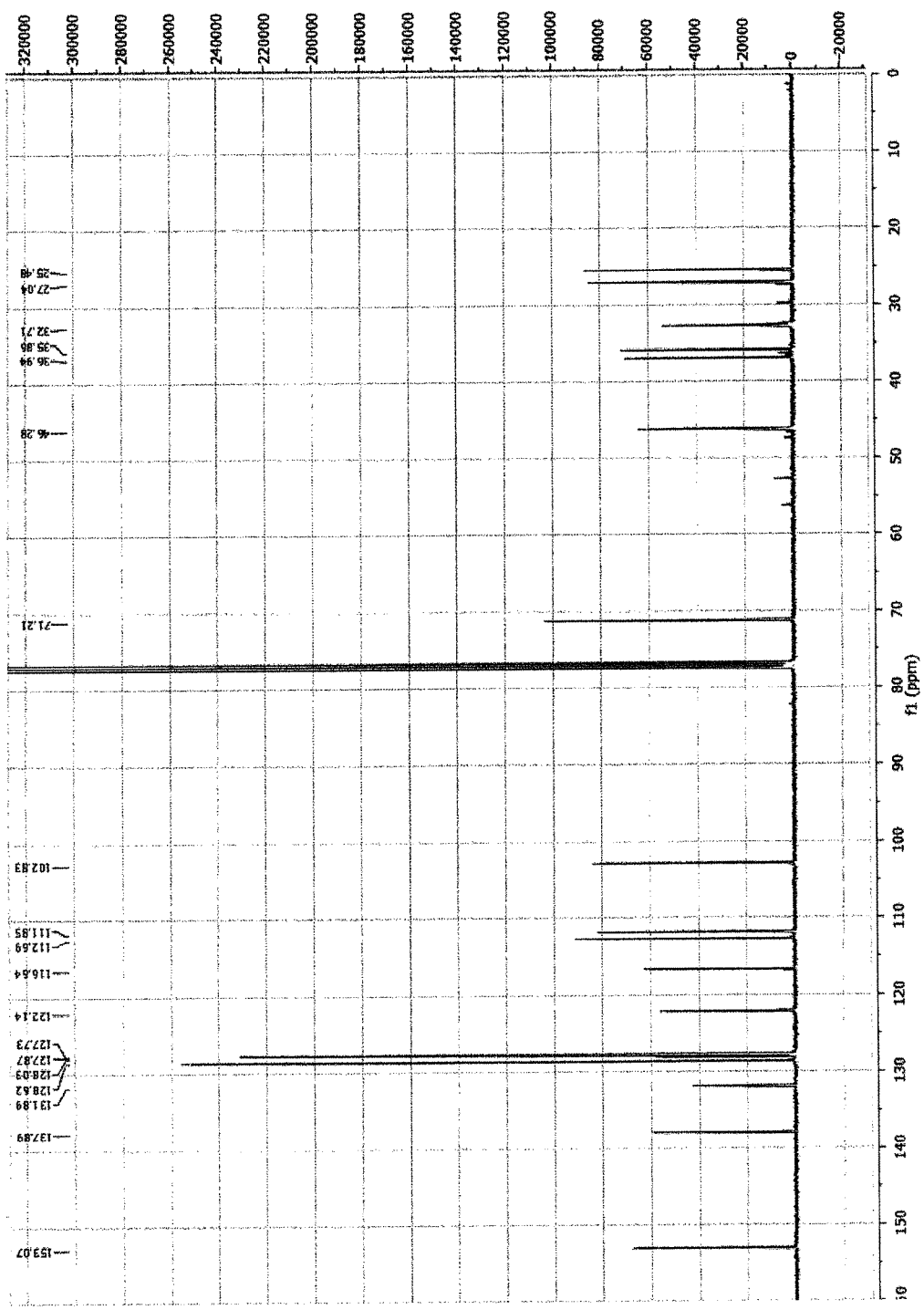

FIG. 5: $^{13}$C-NMR spectrum of homo-5-benzyloxyindalpine (homo-5-BOIP); see Example 3.

Figure 6:
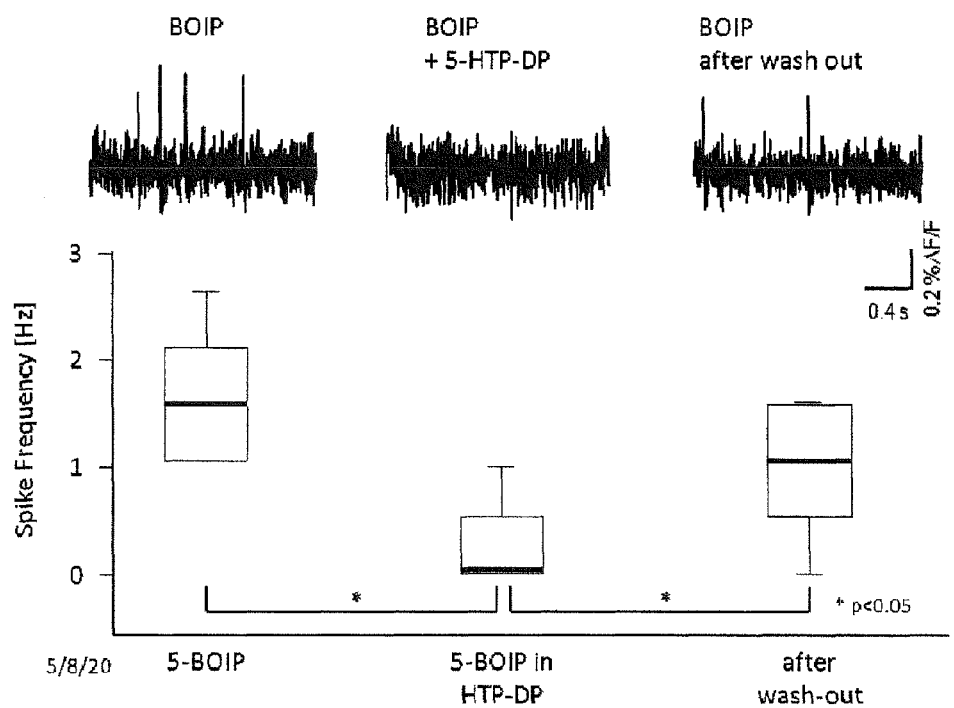

FIG. 6: 5-Benzyloxyindaipine (referred to as "5-BOIP" or "BOIP" in the figure) activates human enteric nerve cells (see Example 4). In the upper left-hand section of the figure, the reaction of a nerve cell to the application of 5-BOIP is shown. The activation of enteric nerve cells by 5-BOIP is almost completely inhibited in the presence of the 5-HT$_{1P}$ receptor antagonist 5-HTP-DP, as shown in the upper central section of this figure. After washing out 5-HTP-DP, freshly added 5-BOIP again induces action potentials, as shown in the upper right-hand section. The action potential (spike) frequencies are shown in the lower section of the figure as medians with 10% and 90% interquartile range (IQR). 5-BOIP induced action potentials at a frequency of 1.6 (1.0/2.1) Hz. This effect was almost completely blocked by the 5-HT$_{1P}$ receptor antagonist 5-HTP-DP, such that the action potential frequency was reduced to 0 (0/0.5) Hz. After washing out the antagonist 5-HTP-DP, the stimulating effect of 5-BOIP recovered and 5-BOIP again induced action potentials at a frequency of 1.0 (0.5/1.6) Hz. Statistically significant differences are marked with an asterisk (*) for $p<0.05$.

Figure 7:
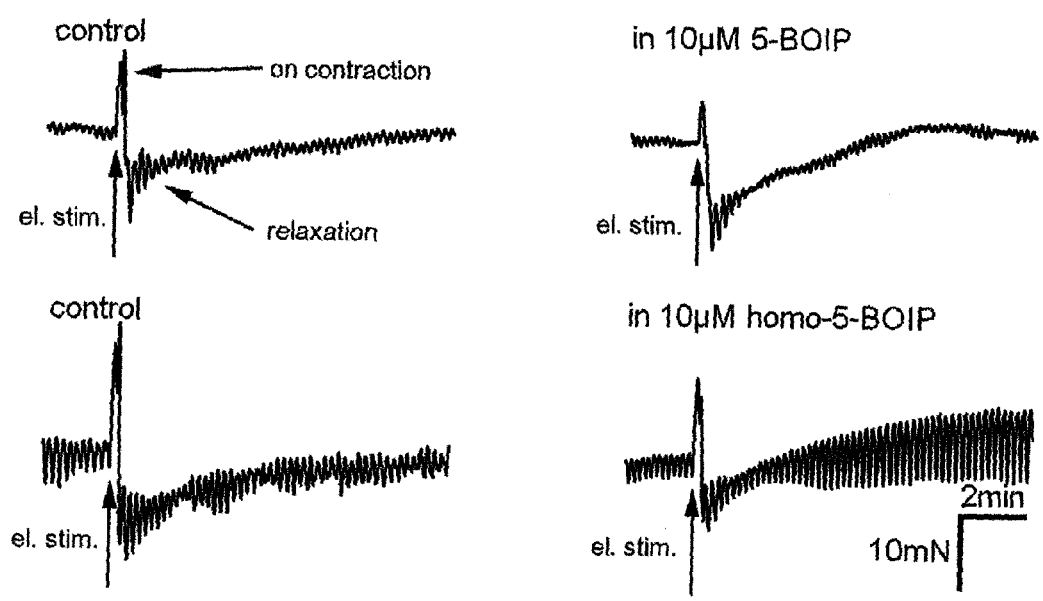

FIG. 7: 5-BOIP and homo-5-BOIP have effects on nerve mediated muscle responses in the guinea pig stomach (see Example 5). On the left side of the figure, the response of two circular muscle strips from the guinea pig stomach to electrical field stimulation (EFS; "el. slim.") is shown. The response consists of an initial, fast contraction ("on contraction") and a relaxation with a longer duration. The parameters for the EFS were chosen to specifically excite neuronal structures in the preparations and have no direct effects on smooth muscle. The response therefore reflects the activation of the enteric nerves and the subsequent release of excitatory and inhibitory neurotransmitters that finally act on receptors on smooth muscle cells. After the addition of 5-BOIP and homo-5-BOIP (10 μM), a second EFS evokes only a reduced "on contraction" in both preparations. This indicates an additional activation of inhibitory neuronal pathways by both substances.

The invention will now be described by reference to the following examples which are merely illustrative and are not to be construed as a limitation of the scope of the present invention. In case of conflict between the chemical structures and the corresponding chemical names indicated in the examples section, the structures depicted herein prevail.

EXAMPLES

Example 1

Synthesis of 5-Benzyloxyindalpine (5-BOIP), route A

5-Benzyloxyindalpine (7) was synthesized in five steps, as shown in Scheme 3 below, starting from commercially available 5-hydroxyindole (1) which was first alkylated with benzylbromide using cesium carbonate and crown ether. The protected 5-benzyloxyindole (2) was coupled in a Grignard reaction with an acid chloride (4) derived from commercially available 1-Cbz-4-piperldineacetic acid (3). Removal of the carbamate protecting group in compound 5 was performed with concentrated HCl to provide compound 6. In a last step, the carbonyl group in compound 6 was transformed into a methylene group in a Wolff-Kishner reduction to yield 5-benzyloxyindalpine (7).

Scheme 3: Synthesis of 5-benzyloxyindalpine (5-BOIP), route A.

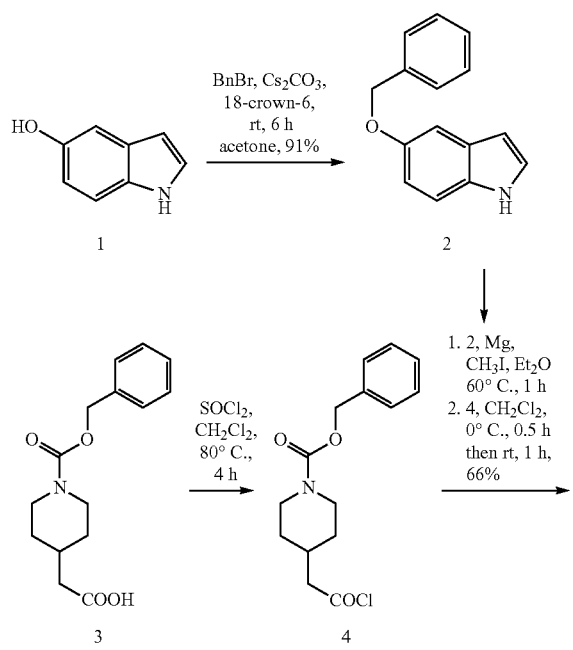

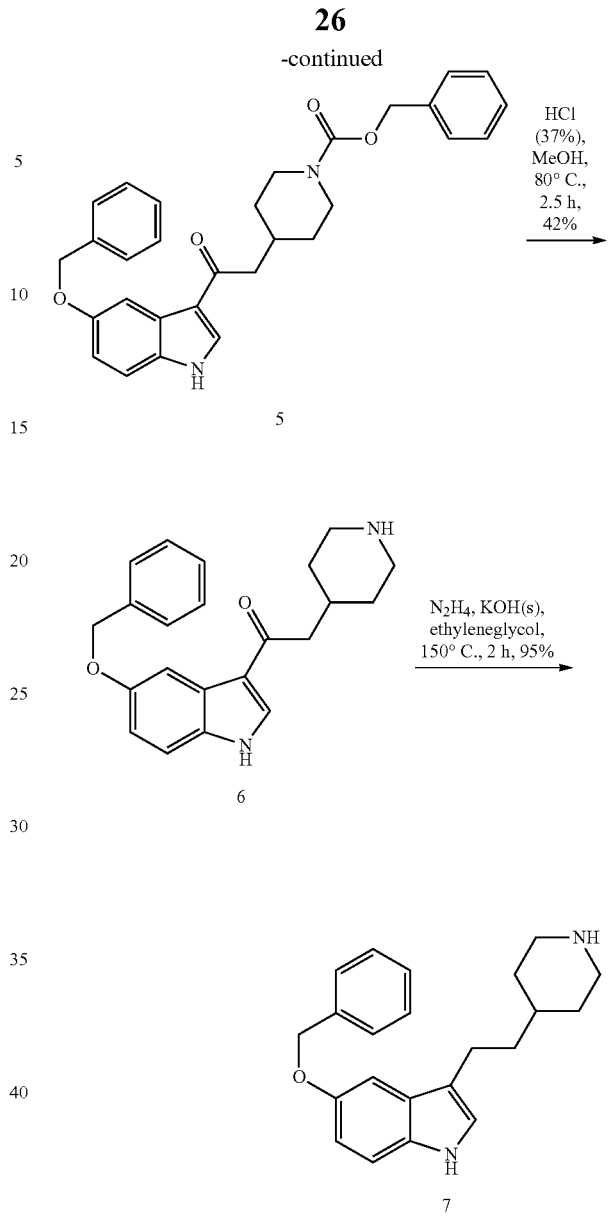

When working with indalpine compounds or their precursors, it is generally recommendable to work under an inert or oxygen-free atmosphere (e.g., a nitrogen or argon atmosphere), to use degassed solutions and to store compounds as solids rather than in aqueous or basic media.

Further general information can be found in: Gueremy C, et al. *J Med Chem.* 1980. 23(12):1306-10; DE-A-2618152; Branchek T A, et al. *J Neuroscience.* 1988. 8:2582-95; Mitchell N A, et al. *Neurogastroenterol Motil.* 2009. 21(7): 760-e48; Ketcha D M, et al. *J Org Chem.* 1985. 50(26): 5451-57; Ketcha D M, at al. J Org Chem. 1989. 54(18): 4350-56; and Lunn G, at al. *J Org Chem.* 1986. 51:513-17.

The synthesis of 5-benzyloxyindalpine outlined above is described in detail in the following. It should be understood that, in case of conflict between the depicted structural formulae and the corresponding chemical names indicated in this Example, the depicted structures prevail.

Step 1: Synthesis of 5-benzyloxyindole (2)

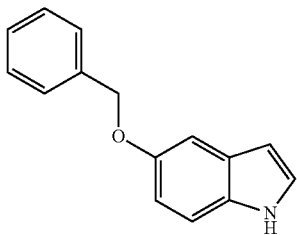

C₁₅H₁₃NO
Exact Mass: 223,10

0.5 g (3.8 mmol) 5-hydroxyindole (1) were dissolved in 5 ml acetone and mixed with 535 μl (4.5 mmol) benzylbromide (BnBr), 2.45 g (7.5 mmol) $Cs_2CO_3$ and 1.2 g (4.5 mmol) 18-crown-6 at room temperature (rt). After stirring for 2.5 to 17 h, preferably for 6 h, the mixture was diluted with water, smoothly acidified with 1 M HCl and extracted three times with $CH_2Cl_2$. The combined organic layers were dried with $Na_2SO_4$, filtered and evaporated. The crude product was purified by flash chromatography ($SiO_2$, cyclohexane-ethyl acetate 4:1) and yielded 762 mg (3.4 mmol, 91%) of a pale yellow solid.

$^1$H-NMR (500 MHz, $CDCl_3$): 8.11 (br, 1 H), 7.52 (d, J=7.5 Hz, 2 H), 7.41 (t, J=7.8 Hz, 2 H), 7.37-7.30 (m, 2 H), 7.22 (d, J=2.3 Hz, 1 H), 7.21 (1, J=2.8 Hz, 1 H), 6.98 (dd, J=8.8 Hz, J=2.4 Hz, 1 H), 6.51 (br, 1 H), 5.15 (s, 2 H).

Step 2: Synthesis of benzyl 4-(2-chloro-2-oxoethyl)piperidine-1-carboxylate (4)

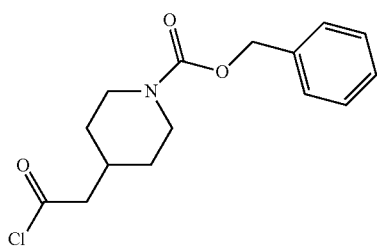

C₁₅H₁₆ClNO₃
Exact Mass: 295,10

502 mg (1.8 mmol) of 2-[1-(benzyloxycarbonyl)piperidin-4-yl]acetic acid (3) were dissolved in anhydrous $CH_2Cl_2$ under argon and mixed with 10 ml $SOCl_2$. After stirring for 4 h at 80° C., the solution was directly evaporated. The residue was mixed three times with anhydrous $CH_2Cl_2$ and evaporated. The residue was further mixed three times with anhydrous toluene and evaporated in vacuo to yield 535 mg (1.8 mmol, 99%) of a white solid. The product was used in the next step without further purification.

Step 3: Synthesis of benzyl 4-[2-(5-(benzyloxy)-1H-indol-3-yl)-2-oxoethyl]piperidine-1-carboxylate (5)

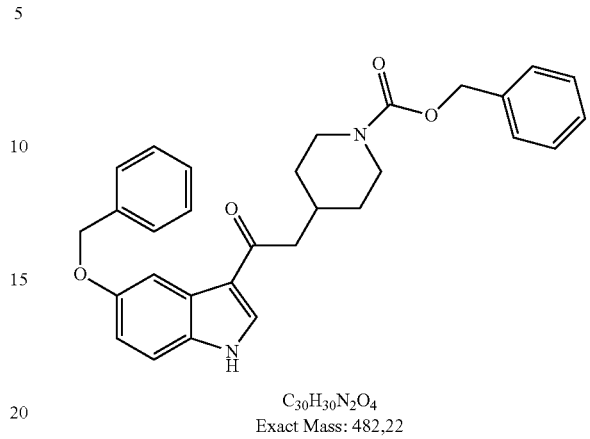

C₃₀H₃₀N₂O₄
Exact Mass: 482,22

110 mg (4.5 mmol) Mg and few crystals $I_2$ were mixed with 10 ml dry diethyl ether ($Et_2O$) and stirred for 10 min at 60° C. under argon atmosphere. 283 μl (4.5 mmol) of $CH_3I$ in 10 ml dry $Et_2O$ were added dropwise at 60° C. and the mixture was stirred for further 2.5 h at 60° C. The mixture was cooled to room temperature and 485 mg (2.2 mmol) of compound 2 in 10 ml dry $Et_2O$ were added dropwise. After subsequent stirring for 1 h at 60° C., the solution was cooled to 0° C. and 535 mg (1.8 mmol) of compound 4 in 10 ml anhydrous $CH_2Cl_2$ were added dropwise (yellow suspension). After stirring for 0.5 h at 0° C. and 1 h at room temperature, the solution was diluted with water, acidified with 1 M HCl (yellow) and extracted three times with $CH_2Cl_2$. The combined organic layers were dried with $Na_2SO_4$, filtered and evaporated in vacuo. The crude yellow product was purified by flash chromatography ($SiO_2$, $CH_2Cl_2$-MeOH 9:1) to yield 574 mg (1.2 mmol, 66%) of a white solid.

$^1$H-NMR (500 MHz, $CDCl_3$): 9.84 (br, 1 H), 8.39 (d, J=3.3 Hz, 1 H), 7.95 (d, J=2.4 Hz, 1 H), 7.75 (d, J=7.3 Hz, 2 H), 7.50-7.36 (m, 10 H), 7.35-7.25 (m, 3 H), 6.98 (dd, J=8.8 Hz, J=2.5 Hz, 1 H), 5.54 (s, 2 H), 5.12 (s, 2 H), 4.62 (s, 2 H), 3.65 (d, J=12.3 Hz, 2 H), 3.10-3.00 (m, 4 H), 2.54 (q, J=13.4 Hz, 2 H), 2.02 (br, 1 H), 1.68 (d, J=13.8 Hz, 2 H)

Step 4: Synthesis of 1-[5-(benzyloxy)-1H-indol-3-yl]-2-(piperidin-4-yl)ethanone (6)

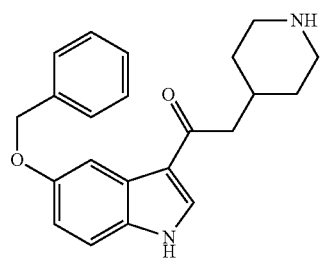

C₂₂H₂₄N₂O₂
Exact Mass: 348,18

574 mg (1.2 mmol) of compound 5 were dissolved in 5 ml MeOH and 5 ml HCl (37%) and stirred for 2.5 h at 80° C. The mixture was cooled to room temperature and directly evaporated in vacuo to yield 184 mg (0.5 mmol, 42%) of a slight pink solid.

$^1$H-NMR (500 MHz, CDCl$_3$): 7.55 (s, 1 H), 7.42 (d, J=7.3 Hz, 2 H), 7.40-7.25 (m, 5 H), 6.83 (dd, J=8.7 Hz, J=2.9 Hz, 1 H), 6.71-6.68 (m, 2 H), 5.00 (s, 2 H), 3.62 (s, 2 H), 3.50 (s, 1 H), 2.93 (d, J=10.7 Hz, 2 H), 2.59 (d, J=6.5 Hz, 2 H), 2.06 (br, 2 H), 1.64-1.52 (m, 2 H), 1.37 (q, J=9.4 Hz, 2 H)

Step 5: Synthesis of 5-benzyloxyindalpine (7)

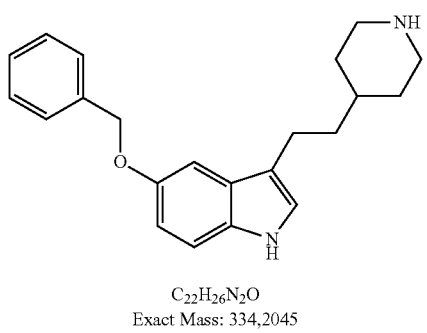 [SMILES: c1ccc(COc2ccc3[nH]cc(CCC4CCNCC4)c3c2)cc1]

C$_{22}$H$_{26}$N$_2$O
Exact Mass: 334,2045

184 mg (0.5 mmol) of compound 6 were dissolved in 10 ml ethylene glycol, mixed with 2 ml N$_2$H$_4$.H$_2$O and 1 g (17.8 mmol) solid KOH, and stirred for 2 h at 150° C. The solution was cooled to room temperature, diluted with water and extracted three times with ethyl acetate. The combined organic layers were dried with Na$_2$SO$_4$, filtered and evaporated in vacuo. The crude product was purified by flash chromatography (SiO$_2$, CH$_2$Cl$_2$-MeOH 7:3) to yield 130 mg (0.5 mmol, 95%) of a brown solid. A portion of the crude brown solid was further purified by semi-preparative HPLC (Purospher STAR, 250×10 mm, RP-8 select-B) to yield 20 mg of a pale brown solid.

$^1$H-NMR (400 MHz, d4-MeOD): 7.99 (s, 1 H), 7.51-7.7.41 (m, 5 H), 7.31 (d, J=7.4 Hz, 1 H), 6.95 (dd, J=8.7 Hz, J=2.5 Hz, 1 H), 6.86 (d, J=2.5 Hz, 1 H), 4.24 (s, 2 H), 3.38 (d, J=11.9 Hz, 2H), 3.27 (br, 2 H), 3.00 (t, J=12.2 Hz, 2 H), 2.66 (d, J=6.8 Hz, 2 H), 2.00-1.90 (br, 1H), 1.85 (d, J=15 Hz, 2 H), 1.48 (q, J=12.6 Hz, 2 H).

When 5-benzyloxyindalpine (7) thus obtained was analyzed by mass spectrometry (MALDI-TOF; matrix: 2,3,4-trihydroxyacetophenone), a mass peak at m/z 242.695 was observed, rather than the expected peak at m/z 334 (FIG. 1). This may be explained by the LASER-induced cleavage of the benzyl group from 5-benzyloxyindalpine and the subsequent photo-oxidation of the cleavage product, resulting in the charged and/or protonated corresponding quinone imine of 5-benzyloxyindalpine.

Example 2

Synthesis of 5-Benzyloxyindalpine (5-BOIP), route B

5-Benzyloxyindalpine (7) was synthesized in five steps, as shown in Scheme 4 below, starting from commercially available 2-(piperidin-4-yl)acetic acid (1), which was first protected at the (secondary) amino group with a carboxybenzyl (Cbz) protecting group. The resulting 2-(N-Cbz-piperidin-4-yl)acetic acid 2 was activated as a carboxylic acid chloride (3) using oxalyl chloride and subsequently coupled with commercially available 5-benzyloxyindole (4) in a Grignard reaction to provide compound 5. Removal of the carbamate protecting group of compound 5 was performed with 5 M HCl in dry ethanol to provide compound 6. In the final step, 5-BOIP (7) was obtained by reducing the carbonyl group of compound 6 with LiAlH$_4$.

Scheme 4: Synthesis of 5-benzyloxyindalpine (5-BOIP), route B.

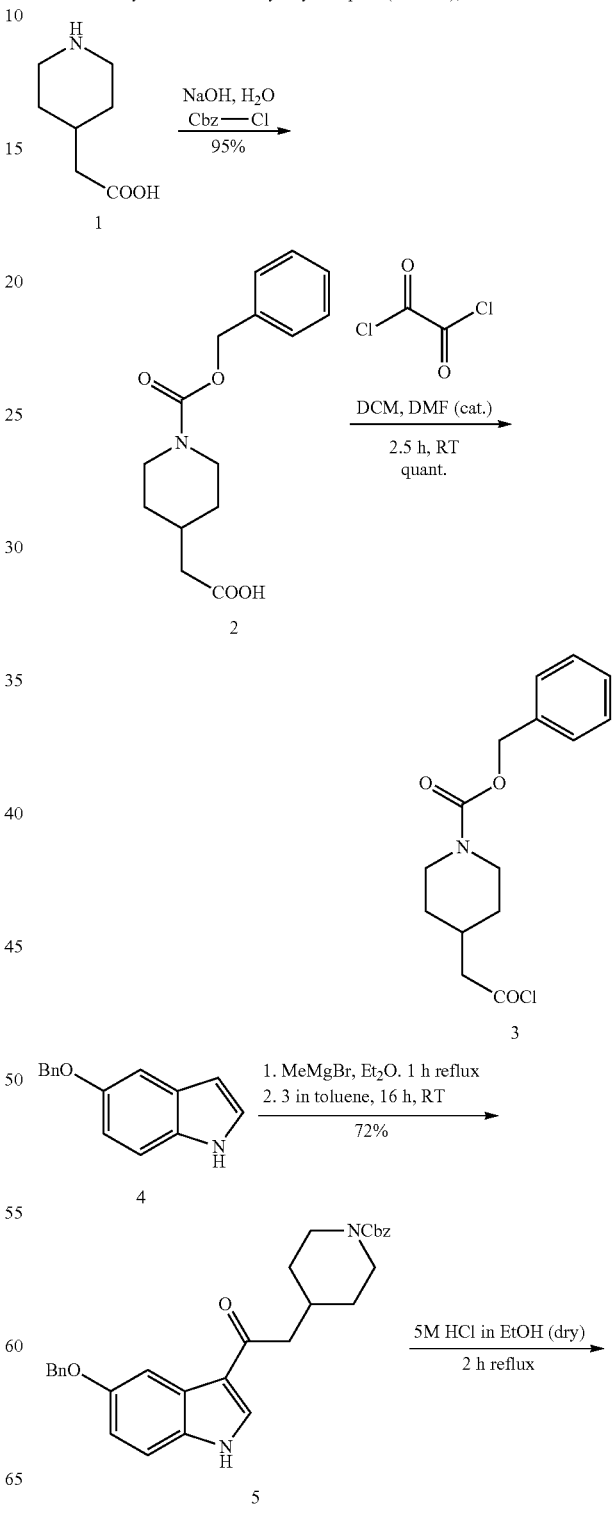

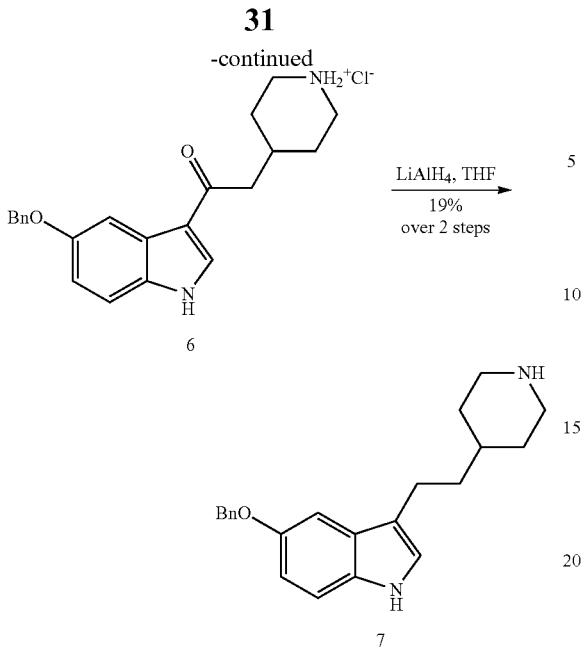

The synthesis of 5-BOIP outlined above is described in detail in the following section.

When working with indalpine compounds or their precursors, it is generally recommendable to work under an inert or oxygen-free atmosphere (e.g., a nitrogen or argon atmosphere), to use degassed solutions, and to store compounds as solids rather than in aqueous or basic media.

Further general information can be found in: Gueremy C, et al. *J Med Chem.* 1980, 23(12); 1306-10; DE-A-2618152; Branchek T A, et al. *J Neuroscience.* 1988, 8:2582-95; Mitchell N A, et al. *Neurogastroenterol Motil.* 2009, 21(7): 760-e48; and Leete E, et al. *Canad J Chem.* 1953, 31:775-84.

Step 1: Synthesis of 2-(N-Cbz-piperidin-4-yl)acetic acid (2)

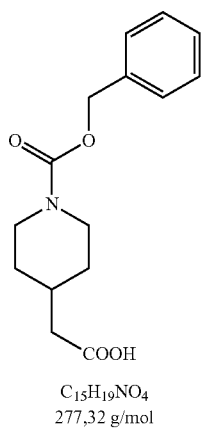 [SMILES: O=C(O)CC1CCN(C(=O)OCc2ccccc2)CC1]

$C_{15}H_{19}NO_4$
277,32 g/mol

To prepare compound 2, a procedure published in DE 4304650 A1 was followed with modifications. 3000 mg (16.7 mmol) 2-(piperidin-4-yl) acetic acid hydrochloride (Iris Biotech, Marktredwitz, Germany) was dissolved in 46 ml of a 1 M solution of NaOH in water and cooled in an ice bath. 3350 µl benzyloxycarbonyl chloride (Cbz-Cl) (23.46 mmol, 4002 mg) were added dropwise over 5 min under stirring. The reaction mixture was allowed to warm to room temperature and stirred for 16 h. The aqueous solution was washed twice with 20 ml of diethyl ether/petroleum ether 4:1 and then acidified with 4 M HCl (aq.) to pH 1. The product of the reaction was extracted with 3×50 ml diisopropyl ether. The combined organic phases were dried with MgSO₄ and evaporated under reduced pressure. Compound 2 was obtained as a colorless solid (4383 mg, 15.8 mmol, 95%).

¹H NMR (400 MHz, Chloroform-d) δ 7.40-7.27 (m, 5H), 5.13 (s, 2H), 4.18 (d, J=13.3 Hz, 2H), 2.81 (t, J=12.8 Hz, 2H), 2.29 (d, J=7.0 Hz, 2H), 1.96 (tp, J=11.2, 3.5 Hz, 1H), 1.75 (d, J=12.1 Hz, 2H), 1.30-1.09 (m, 2H)

Step 2: Synthesis of 2-(N-Cbz-piperidin-4-yl)acetic acid chloride (3)

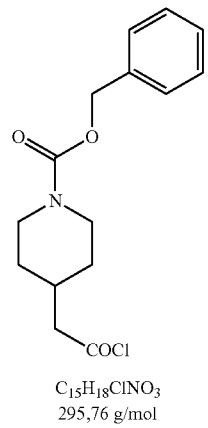 [SMILES: O=C(Cl)CC1CCN(C(=O)OCc2ccccc2)CC1]

$C_{15}H_{18}ClNO_3$
295,76 g/mol

Compound 2 (3000 mg, 10.82 mmol) was dissolved in 30 ml dry dichloromethane (DCM) at room temperature. 1831 µl (21.64 mmol, 2746 mg) oxalyl chloride were added slowly. After stirring the mixture for 30 min, 30 µl dimethylformamide (DMF) were added and stirring was continued for 2 h. Then the solvent was removed under reduced pressure. The remaining material was dried thoroughly under vacuum. Acid chloride 3 was obtained as a colorless, slightly cloudy oil and was used without further purification.

Step 3: Synthesis of benzyl 4-[2-(5-(benzyloxy)-1H-indol-3-yl)-2-oxoethyl]piperidine-1-carboxylate (5)

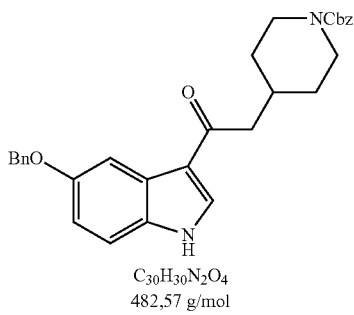 [SMILES: O=C(CC1CCN(C(=O)OCc2ccccc2)CC1)c1c[nH]c2ccc(OCc3ccccc3)cc12]

$C_{30}H_{30}N_2O_4$
482,57 g/mol

A procedure for the preparation of compound 5 can be found in DE 2618152 A1 and Gueremy C, et al. *J Med Chem*. 1980, 23(12):1306-10. 7935 µl of a 3 M solution of methylmagnesium bromide (MeMgBr) in diethyl ether (Et$_2$O) was placed in a 250 ml Schlenk flask. A solution of 2416 mg (10.82 mmol) 5-benzyloxyindole (4) in 40 ml dry diethyl ether was added, and the resulting mixture was stirred for 1 h under reflux. After cooling to 0° C. in an ice bath, a solution of acid chloride 3 in 30 ml dry toluene was added slowly. The reaction mixture was stirred for 30 min at 0° C. and then for 16 h at room temperature. The reaction mixture was diluted with DCM and 1 M HCl (aq.) until all solids were dissolved. The phases were separated and the aqueous layer was extracted twice with 20 ml DCM. The combined organic phases were washed with 2×1 M HCl (aq.), 2× saturated NaHCO$_3$ (aq.) and 1× saturated NaCl (aq.), dried with MgSO$_4$, and evaporated under reduced pressure. The crude product was purified by silica chromatography (eluent petroleum ether/ethyl acetate 2:3, then 1:2). Compound 5 was obtained as a slightly yellow solid (3783 mg, 7.84 mmol, 72%).

$^1$H NMR (400 MHz, Chloroform-d) δ 9.00 (s, 1H), 8.03 (d, J=2.5 Hz, 1H), 7.70 (d, J=3.1 Hz, 1H), 7.50-7.45 (m, 2H), 7.42-7.28 (m, 9H), 7.26 (d, J=3.8 Hz, 1H), 7.00 (dd, J=8.8, 2.5 Hz, 1H), 5.14 (s, 2H), 5.12 (s, 2H), 4.23-4.13 (m, 2H), 2.88-2.76 (m, 2H), 2.71 (d, J=6.9 Hz, 2H), 2.21 (tp, J=11.1, 3.4 Hz, 1H), 1.82-1.71 (m, 2H), 1.20 (ddt, J=12.3, 4.2 Hz, 2H)

$^{13}$C NMR (101 MHz, Chloroform-d) δ 195.19, 155.75, 155.49, 137.41, 137.01, 131.76, 131.49, 128.65-128.61 (m), 128.11, 127.99-127.94 (m), 127.80 (m), 126.35, 118.54, 115.12, 112.39, 105.02, 70.66, 67.16), 46.22, 44.34, 33.13, 32.37

HPLC: Column Purospher RP8e 250×5 mm, gradient 10-100% ACN in H$_2$O+0.1% TFA in 30 min, flow rate 0.6 ml/min; $t_R$=24.77 min MS: calc. [M+H]$^+$=483.22783. found [M+H]$^+$=483.22900.

Step 4: Synthesis of 1-(5-[benzyloxy]-1H-indol-3-yl)-2-(piperidin-4-yl)ethanone hydrochloride (6)

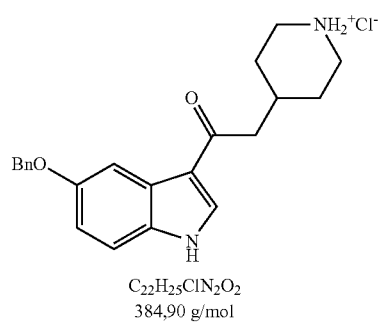

C$_{22}$H$_{25}$ClN$_2$O$_2$
384,90 g/mol

A procedure for the preparation of compound 6 can be found in DE 2618152 A1 and Gueremy C, et al. *J Med Chem*. 1980, 23(12):1306-10. Compound 5 was dissolved in a solution of 5 M HCl in dry ethanol (EtOH). The reaction mixture was stirred for 2 h under reflux. After cooling to room temperature, the solvent was removed under reduced pressure. The remaining material was dissolved in 5 ml EtOH. 45 ml diethyl ether was added, causing precipitation of the desired product together with small amounts of the debenzylated derivative and red-colored impurities. The precipitate was filtered off, washed with diethyl ether, and dried under vacuum. The crude product (1600 mg) was used without further purification.

HPLC: Column Purospher RP8e 250×5 mm, gradient 10-100% ACN in H$_2$O+0.2% AcOH in 30 min, flow rate 0.6 ml/min; $t_R$=11.41 min MS: calc. [M+H]$^+$=349.19105. found [M+H]$^+$=349.19114.

Step 5: Synthesis of 5-(benzyloxy)-3-(2-(piperidin-4-yl)ethyl)-1H-indole (5-benzyloxyindalpine, 5-BOIP) (7)

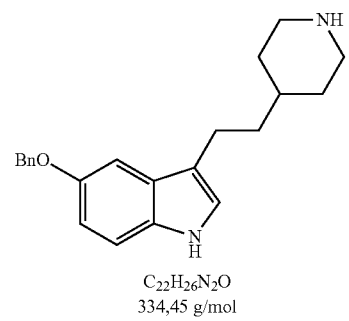 [SMILES: c1ccc(COc2ccc3[nH]cc(CCC4CCNCC4)c3c2)cc1]

C$_{22}$H$_{26}$N$_2$O
334,45 g/mol

Compound 6 (600 mg, 1.56 mmol) was suspended in 50 ml tetrahydrofuran (THF). A suspension of 296 mg (7.8 mmol) LiAlH$_4$ in 20 ml THF was added slowly at room temperature and stirred for 1 h at 60° C. The reaction mixture was cooled to room temperature and the reaction was quenched by slow addition of water. Solid components were filtered off. The filtrate was treated with 50 ml of a saturated solution of NaHCO$_3$ in water and extracted 4× with DCM. The combined organic phases were washed with 1×100 ml water and 1×100 ml brine, dried with MgSO$_4$, and evaporated under reduced pressure. The remaining material was dissolved in EtOH and purified by semipreparative HPLC (column Purospher RP8e, 250×10 mm). 5-BOIP (7) was obtained as a slightly yellowish solid (98 mg, 29 µmol, 19% over 2 steps).

An $^1$H NMR spectrum and a $^{13}$C NMR spectrum of 5-BOIP (7) are shown in FIGS. 2 and 3, respectively.

$^1$H NMR (400 MHz, Methanol-d4) δ 7.48-7.42 (m, 2H), 7.39-7.33 (m, 2H), 7.31-7.25 (m, 1H), 7.22 (d, J=8.7 Hz, 1H), 7.05 (d, J=2.4 Hz, 1H), 6.97 (s, 1H), 6.83 (dd, J=8.8, 2.4 Hz, 1H), 5.08 (s, 2H), 3.15 (dt, J=12.7, 3.2 Hz, 2H), 2.76-2.63 (m, 4H), 1.88-1.79 (m, 2H), 1.67-1.58 (m, 2H), 1.59-1.42 (m, 1H), 1.33-1.19 (m, 2H)

$^{13}$C NMR (101 MHz, Methanol-d4) δ 153.76, 139.51, 133.74, 129.42 (2×), 129.01, 128.67, 128.63 (2×), 123.59, 116.01, 113.11, 112.82, 103.54, 72.22, 46.36, 38.15, 35.69, 32.18, 22.99

HPLC: Column Purospher RP8e 250×5 mm, gradient 10-100% ACN in H$_2$O+0.2% AcOH in 30 min, flow rate 0.6 ml/min; $t_R$=12.63 min MS: calc. [M+H]$^+$=335.21179. found [M+H]$^+$=335.21276.

Example 3

Synthesis of Homo-5-benzyloxyindalpine (homo-5-BOIP)

Homo-5-benzyloxyindalpine (homo-5-BOIP), i.e. 5-(benzyloxy)-3-(3-[piperidin-4-yl]propyl)-1H-indole (13), was synthesized similarly to route B described in Example 2 for 5-BOIP, starting from commercially available 3-(piperidin-4-yl)propionic acid (8) as shown in Scheme 5 below.

Scheme 5: Synthesis of homo-5-benzyloxyindalpine (homo-5-BOIP).

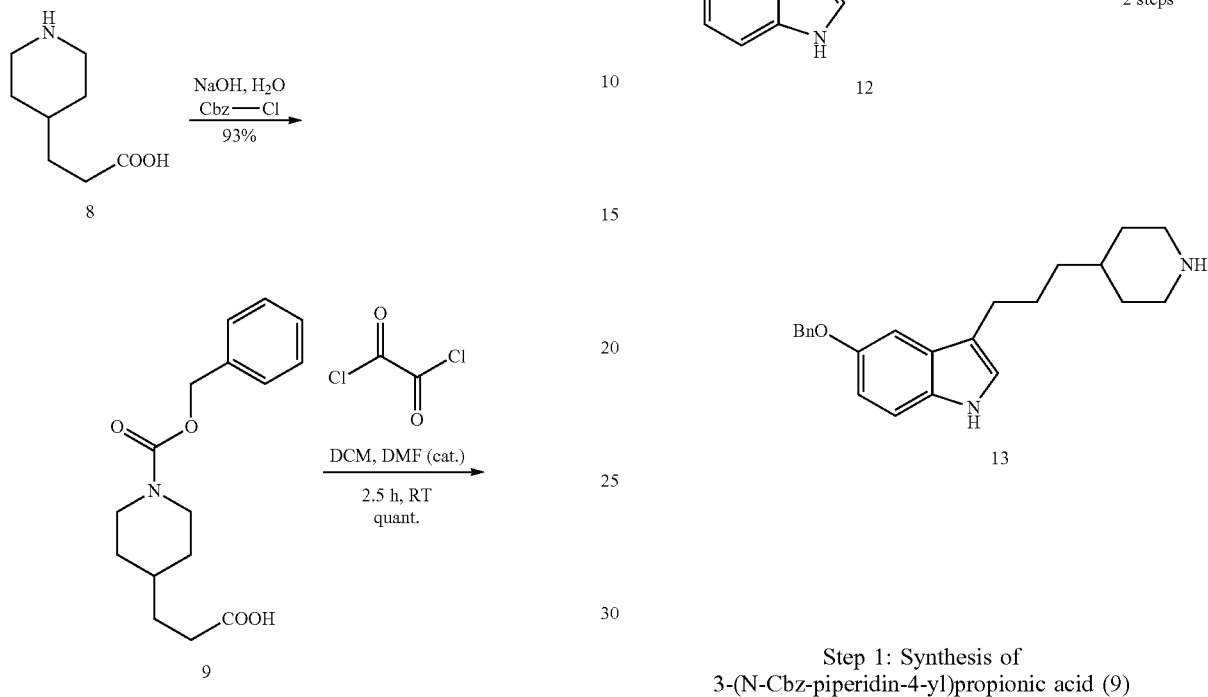

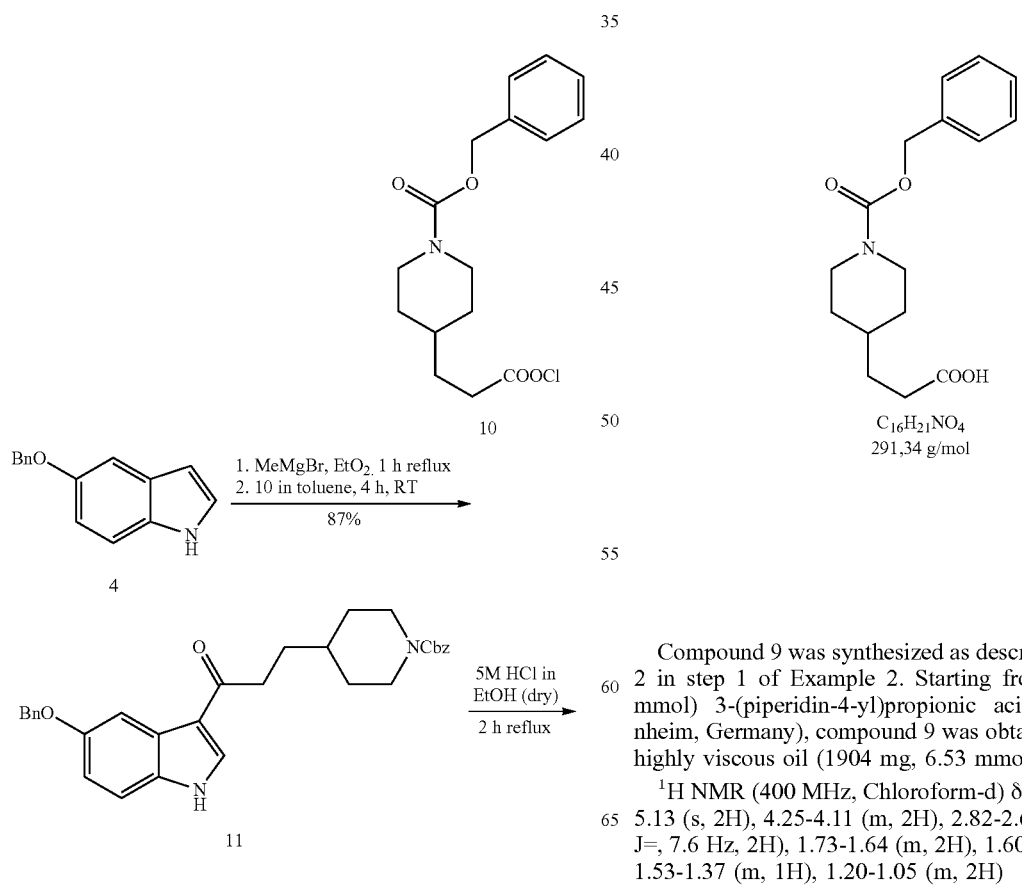

Step 1: Synthesis of 3-(N-Cbz-piperidin-4-yl)propionic acid (9)

Compound 9 was synthesized as described for compound 2 in step 1 of Example 2. Starting from 1100 mg (7.00 mmol) 3-(piperidin-4-yl)propionic acid (CHESS, Mannheim, Germany), compound 9 was obtained as a colorless, highly viscous oil (1904 mg, 6.53 mmol, 93%).

$^1$H NMR (400 MHz, Chloroform-d) δ 7.39-7.27 (m, 5H), 5.13 (s, 2H), 4.25-4.11 (m, 2H), 2.82-2.68 (m, 2H), 2.37 (t, J=, 7.6 Hz, 2H), 1.73-1.64 (m, 2H), 1.60 (q, J=7.3 Hz, 2H), 1.53-1.37 (m, 1H), 1.20-1.05 (m, 2H)

Step 2: Synthesis of 2-(N-Cbz-piperidin-4-yl)propionic acid chloride (10)

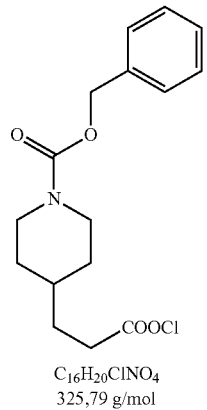

C₁₆H₂₀ClNO₄
325,79 g/mol

Compound 10 was synthesized as described for compound 3 in step 2 of Example 2, starting from 1900 mg (6.53 mmol) compound 9. Compound 10 was obtained as a colorless, slightly cloudy oil and was used without further purification.

Step 3: Synthesis of benzyl 4-(3-[5-(benzyloxy)-1H-indol-3-yl]-3-oxopropyl)piperidine-1-carboxylate (11)

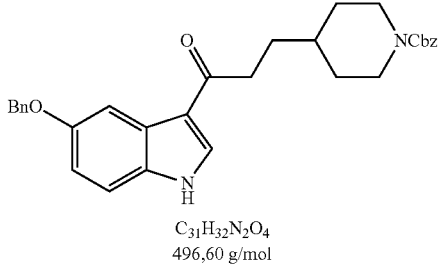 [SMILES: O=C(CCC1CCN(C(=O)OCc2ccccc2)CC1)c1c[nH]c2ccc(OCc3ccccc3)cc12]

C₃₁H₃₂N₂O₄
496,60 g/mol

Compound 11 was synthesized as described for compound 5 in step 3 of Example 2, starting from 6.53 mmol carboxylic acid chloride 10. The crude product was purified by silica chromatography (eluent petroleum ether/ethyl acetate 1:1, then 1:2). Compound 11 was obtained as a slightly yellow solid (2815 mg, 5.67 mmol, 87%).

$^1$H NMR (400 MHz, Chloroform-d) δ 9.33 (d, J=3.3 Hz, 1H), 8.02 (d, J=2.5 Hz, 1H), 7.74 (d, J=3.1 Hz, 1H), 7.48-7.43 (m, 2H), 7.41-7.34 (m, 6H), 7.33-7.29 (m, 2H), 7.28-7.24 (m, 1H), 6.99 (dd, J=8.9, 2.5 Hz, 1H), 5.15 (s, 2H), 5.10 (s, 2H), 4.19-4.15 (m, 2H), 2.85 (t, J=7.5 Hz, 2H), 2.82-2.71 (m, 2H), 1.84-1.64 (m, 4H), 1.54 (tp, J=10.9, 3.4 Hz, 1H), 1.15 (qd, J=12.5, 4.3 Hz, 2H)

$^{13}$C NMR (101 MHz, Chloroform-d) δ 196.31, 155.63, 155.48, 137.39, 136.98, 131.66, 131.58, 128.61 (m), 128.08, 127.96, 127.88, 127.77, 126.43, 117.65, 114.89, 112.45, 105.03, 70.65, 67.14, 44.31, 36.53, 35.56, 32.07, 31.58

HPLC: Column Purospher RP8e 250×5 mm, gradient 10-100% ACN in H₂O+0.1% TFA in 30 min, flow rate 0.6 ml/min; $t_R$=25.97 min MS: calc. [M+H]⁺=497.24348. found [M+H]⁺=497.24557.

Step 4: Synthesis of 1-(5-[benzyloxy]-1H-indol-3-yl)-3-(piperidin-4-yl)propan-1-one (12)

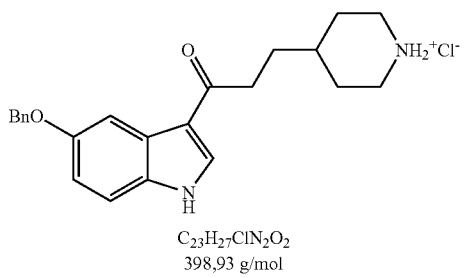

C₂₃H₂₇ClN₂O₂
398,93 g/mol

Compound 12 was synthesized as described for compound 6 in step 4 of Example 2. Starting from 1000 mg (2.01 mmol) compound 11, 725 mg of crude compound 12 were obtained, containing small amounts of debenzylated side product and red-colored impurities.

HPLC: Column Purospher RP8e 250×5 mm, gradient 10-100% ACN in H₂O+0.2% AcOH in 30 min, flow rate 0.6 ml/min; $t_R$=11.94 min MS: calc. [M+H]⁺=363.20670. found [M+H]⁺=363.20696.

Step 5: Synthesis of 5-(benzyloxy)-3-(3-[piperidin-4-yl]propyl)-1H-indole (homo-5-BOIP) (13)

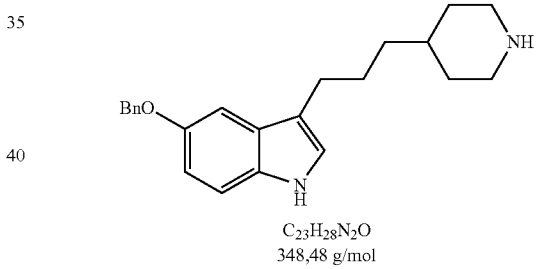

C₂₃H₂₈N₂O
348,48 g/mol

Compound 13 was prepared as described for compound 7 in step 5 of Example 2, starting from 600 mg (1.50 mmol) ketone 12. After purification by HPLC (column Purospher RP8e, 250×10 mm), compound 13 was obtained as a slightly yellow solid (isolated: 43 mg, 12.3 μmol, 8.2% over 2 steps; total yield: approx. 20%).

An $^1$H NMR spectrum and a $^{13}$C NMR spectrum of homo-5-BOIP (13) are shown in FIGS. 4 and 5, respectively.

$^1$H NMR (400 MHz, Chloroform-d) δ 7.52-7.46 (m, 2H), 7.42-7.36 (m, 2H), 7.35-7.29 (m, 1H), 7.24 (d, J=8.8 Hz, 1H), 7.12 (d, J=2.4 Hz, 1H), 6.96-6.90 (m, 2H), 5.12 (s, 2H), 3.14 (dt, J=12.7, 3.0 Hz, 2H), 2.72-2.66 (m, 2H), 2.68-2.56 (m, 2H), 1.76-1.65 (m, 4H), 1.47-1.29 (m, 3H), 1.29-1.13 (m, 2H)

$^{13}$C NMR (101 MHz, Chloroform-d) δ 153.07, 137.89, 131.89, 128.62 (2×), 128.03, 127.87, 127.73 (2×), 122.14, 116.64, 112.69, 111.85, 102.83, 71.21, 46.28, 36.94, 35.86, 32.71, 27.04, 25.48

HPLC: Column Purospher RP8e 250×5 mm, gradient 10-100% ACN in H₂O+0.2% AcOH in 30 min, flow rate 0.6 ml/min; $t_R$=13.41 min MS: calc. [M+H]⁺=349.22744. found [M+H]⁺=349.22803.

Example 4

5-Benzyloxyindalpine (5-BOIP) Acts as an Agonist of the 5-HT$_{1P}$ Receptor in a Neuronal Tissue Assay The effect of 5-BOIP was tested on freshly dissected submucous plexus preparations from surgical resections of human intestine. Samples were taken from macroscopically unaffected areas. Procedures were approved by the ethics committees of the Technical University Munich (1748/07 and 2595/09). Segments were dissected in ice cold Krebs solution to obtain mucosa/submucosa preparations containing the inner submucous plexus preparations for the imaging experiments.

In order to image the activity of enteric neurons using voltage sensitive dyes, the human submucous plexus preparations were placed into a recording chamber which was continuously perfused at 37° C. with oxygenated Krebs solution containing 117 mM NaCl, 4.7 mM KCl, 1.2 mM MgCl$_2$, 1.2 mM NaH$_2$PO$_4$, 20 mM NaHCO$_3$, 2.5 mM CaCl$_2$, 11 mM glucose (pH 7.4). The neuroimaging set-up allowed to monitor membrane potential changes and changes in intracellular Ca$^{2+}$ [Ca]$_i$ transients in all cells of a given ganglion. To study membrane potential changes, individual ganglia were stained with the voltage-sensitive dye Di-8-ANEPPS (20 µM; Molecular Probes, Eugene, Oreg., USA) via intraganglionic application through a microejection pipette.

The imaging experiments were conducted on an inverted microscope (Zeiss Axio Observer.A1; Munich, Germany) equipped with the NeuroCCD system, consisting of a fast CCD camera (80×80 pixels) and the Neuroplex software for data acquisition and analysis (RedShirtImaging, Decatur, Ga., USA). To detect Di-8-ANEPPS a modified Cy3 filterset (545±15 nm excitation, 565 nm dichroic mirror, 580 nm barrier; Ahf Analysentechnik, Tübingen, Germany) was used. A green LED (LE T S2W, Osram, Munich, Germany) was used to excite Di-8-ANEPPS. Visualization of the ganglia and recording of signals were done with a ×100 or ×40 objective (NA=1.35, Olympus, Hamburg, Germany). The imaging set-up allowed to measure relative changes in the fluorescence (ΔF/F), which is for Di-8-ANEPPS linearly related to changes in the membrane potential. Frame rate to detect action potentials was 1 kHz. The overlay of signals and ganglion images allowed the analysis of the responses of individual cells.

5-BOIP was prepared at a stock solution of 100 mM. For controlled local application fine glass capillaries were filled with 50 µM 5-BOIP and positioned just above a ganglion. 5-BOIP was microejected for 400 ms via pressure pulse onto the ganglion. Previously performed calibration of the pressure ejection application method revealed that any substance will be diluted by a factor of 8 once it reaches the ganglion surface. Since G protein coupled receptor activation takes several seconds, the recordings were started after a period of 2 s. In preliminary experiments it was verified that there was no immediate effect of 5-BOIP that would begin with the ejection application or directly thereafter.

The specificity of 5-BOIP effects was tested against the 5-HT$_1$ antagonist 5-hydroxytryptophan dipeptide (5-HTP-DP). For these experiments a control ejection of 5-BOIP was first applied and the ejection was repeated during a 20 min bath application of 10 µM 5-HTP-DP (addition to the tissue superfusing Krebs solution).

It was found that 5-BOIP, when applied to the ganglia, induces action potentials and, thus, activates human enteric nerve cells, as also shown in the left section of FIG. 6. The activation of enteric nerve cells by 5-BOIP is almost completely inhibited in the presence of the 5-HT$_{1P}$ receptor antagonist 5-HTP-DP (see the central section of FIG. 6), while 5-BOIP freshly added after having washed out 5-HTP-DP again induces action potentials (see the right section of FIG. 6).

These results indicate that 5-BOIP stimulates human enteric nerve cells by agonization of the 5-HT$_{1P}$ receptor which is known to play a key role in the initiation of the peristaltic reflex in the intestine. The compounds of formula (I) and in particular the compound 5-BOIP can thus be used to promote intestinal peristalsis and thereby enhance intestinal motility. Accordingly, the compounds of the present invention are useful as therapeutic agents for the treatment or prevention of gastrointestinal diseases/disorders and, in particular, for relieving gastrointestinal symptoms. In the proximal stomach, the compounds evoke muscle relaxation, thereby improving the gastric accommodation reflex. Accordingly, the compounds of the present invention are useful as therapeutic agents for the treatment or prevention of diseases associated with an impaired gastric accommodation.

Example 5

The Compounds 5-BOIP and Homo-5-BOIP have Relaxatory Effects on Nerve Mediated Muscle Responses in the Guinea Pig Stomach The effects of 5-BOIP and homo-5-BOIP were tested in tissue preparations from the guinea pig stomach. After sacrificing the guinea pigs, the stomach was removed and immediately placed in ice-cold oxygenated Krebs solution. The stomach was opened along the greater curvature, thoroughly washed and pinned mucosal side up in Sylgard-coated Petri dishes. The mucosa was then carefully removed. Muscle strips (1.5 cm$^2$) were cut parallel to the circular muscle and mounted in 25 ml organ baths where they were maintained in oxygenated Krebs solution at 37° C. One edge of each muscle strip was attached to an isometric tension transducer (PowerLab, AD Instruments, Spechbach, Germany).

After mounting in the organ baths, tissues were equilibrated with a preload set at 15 mN for 45 min. Then, electrical field stimulations (EFS) were performed (constant current, 100 mA, pulse frequency 10 Hz, pulse width of 0.5 ms, 10 s). With the chosen parameters for the EFS, only the neuronal tissue in the preparation was stimulated without having a direct effect on the smooth muscle. The tissues used in the experiments responded to the EFS with an initial contraction ("on contraction") followed by an inhibition of muscle contractility ("relaxation"). Since only the neuronal tissue was stimulated, this response reflects the activation of the enteric nerves and the subsequent release of excitatory and inhibitory neurotransmitters that finally act on receptors on smooth muscle cells.

After reaching stable responses to the EFS, 5-BOIP and homo-5-BOIP were added to the organ baths at a final concentration of 10 µM. After 20 min, another EFS was applied. The responses to the EFS under control conditions and in the presence of 5-BOIP or homo-5-BOIP were analyzed later.

As shown in FIG. 7, 5-BOIP as well as homo-5-BOIP clearly reduced the "on contraction" in response to the EFS. Because the EFS specifically excited neuronal tissue, this reduction is interpreted as an additional activation of inhibitory neuronal pathways by 5-BOIP and homo-5-BOIP.

These results indicate that the compounds of formula (I) and in particular 5-BOIP and homo-5-BOIP promote a relaxation of gastric smooth muscle cells which is mediated by the activation of inhibitory neuronal pathways in the stomach. The compounds of the present invention thus improve gastric accommodation and, consequently, can be used for the treatment or prevention of gastrointestinal diseases/disorders and, in particular, for relieving gastrointestinal symptoms.

The invention claimed is:

1. A compound of formula (I-1)

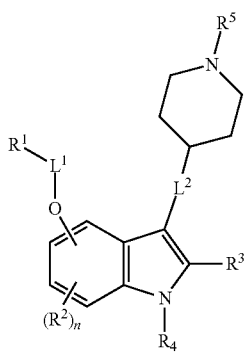

(I-1)

wherein:
$L^1$ is $C_{1-4}$ alkylene;
$L^2$ is $C_{2-4}$ alkylene;
$R^1$ is aryl or heteroaryl, wherein said aryl or said heteroaryl is optionally substituted with one or more groups independently selected from the group consisting of $C_{1-4}$ alkyl, halogen, —$CF_3$, —CN, —OH, —O($C_{1-4}$ alkyl), —SH, —S($C_{1-4}$ alkyl), —$NH_2$, —NH($C_{1-4}$ alkyl), and —N($C_{1-4}$ alkyl)($C_{1-4}$ alkyl);
each $R^2$ is independently selected from the group consisting of $C_{1-4}$ alkyl, halogen, —$CF_3$, —CN, —OH, —O($C_{1-4}$ alkyl), —SH, —S($C_{1-4}$ alkyl), —$NH_2$, —NH($C_{1-4}$ alkyl), and —N($C_{1-4}$ alkyl)($C_{1-4}$ alkyl);
$R^3$ is selected from the group consisting of hydrogen, $C_{1-4}$ alkyl, halogen, —$CF_3$, —CN, —OH, —O($C_{1-4}$ alkyl), —SH, —S($C_{1-4}$ alkyl), —$NH_2$, —NH($C_{1-4}$ alkyl), and —N($C_{1-4}$ alkyl)($C_{1-4}$ alkyl);
$R^4$ is selected from the group consisting of hydrogen, $C_{1-4}$ alkyl, and —CO($C_{1-4}$ alkyl);
$R^5$ is selected from the group consisting of hydrogen, $C_{1-4}$ alkyl, and —CO($C_{1-4}$ alkyl); and
n is 0, 1, 2 or 3;
or a pharmaceutically acceptable salt or solvate thereof.

2. The compound of claim 1, wherein $L^1$ is —$CH_2$— or —$CH_2CH_2$—.

3. The compound of claim 1, wherein $L^2$ is —$CH_2CH_2$— or —$CH_2CH_2CH_2$—.

4. The compound of claim 1, wherein $L^2$ is —$CH_2CH_2$—.

5. The compound of claim 1, wherein $R^1$ is phenyl optionally substituted with one or more groups independently selected from the group consisting of $C_{1-4}$ alkyl, halogen, —$CF_3$, —CN, —OH, —O($C_{1-4}$ alkyl), —SH, —S($C_{1-4}$ alkyl), —$NH_2$, —NH($C_{1-4}$ alkyl), and —N($C_{1-4}$ alkyl)($C_{1-4}$ alkyl).

6. The compound of claim 1, wherein $R^1$ is phenyl.

7. The compound of claim 1, wherein $R^3$, $R^4$ and $R^5$ are each hydrogen.

8. The compound of claim 1, wherein the moiety —O-$L^1$-$R^1$ is bound to position 5 or 6 of the indole ring of the compound of formula (I).

9. The compound of claim 1, wherein said compound is a compound of formula (II-1)

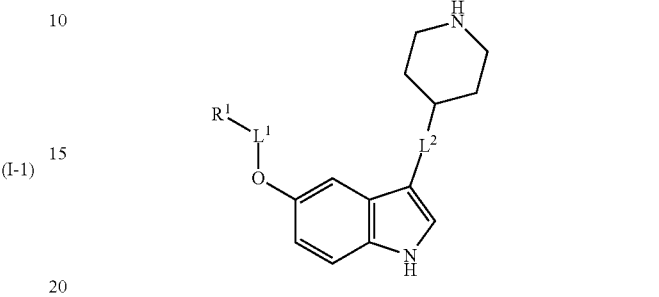

(II-1)

wherein:
$L^1$ is —$(CH_2)_{1-4}$—;
$L^2$ is —$CH_2CH_2$— or —$CH_2CH_2CH_2$—; and
$R^1$ is phenyl optionally substituted with one or more groups independently selected from the group consisting of $C_{1-4}$ alkyl, halogen, —$CF_3$, —CN, —OH, —O($C_{1-4}$ alkyl), —SH, —S($C_{1-4}$ alkyl), —$NH_2$, —NH($C_{1-4}$ alkyl), and —N($C_{1-4}$ alkyl)($C_{1-4}$ alkyl);

or a pharmaceutically acceptable salt or solvate thereof.

10. The compound of claim 1, wherein said compound has one of the following structures:

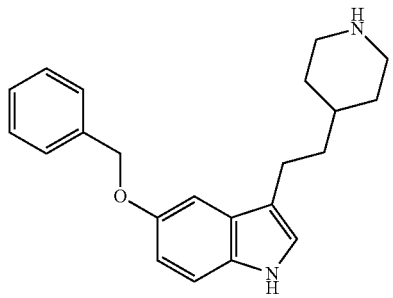

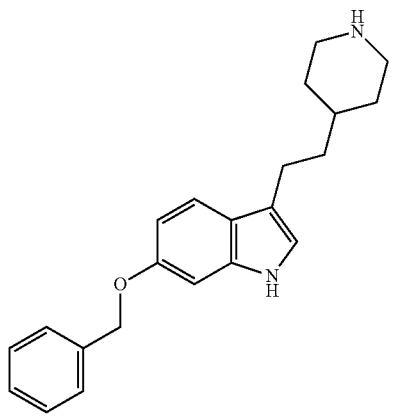

-continued

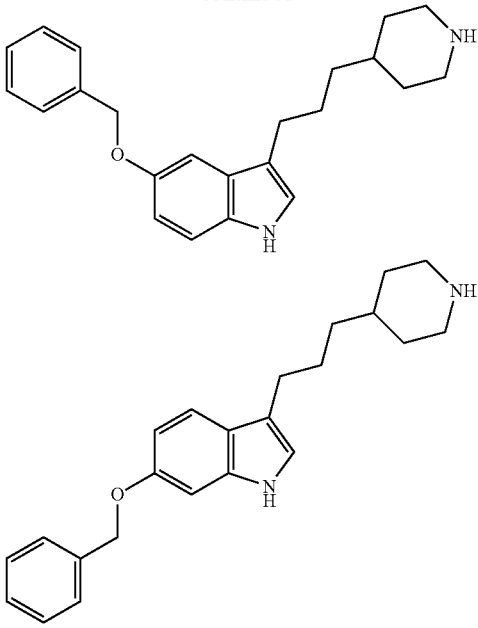

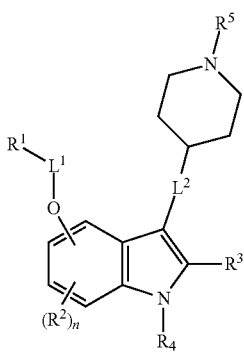

or a pharmaceutically acceptable salt or solvate thereof.

11. A pharmaceutical composition comprising a compound of formula (I) or a pharmaceutically acceptable salt or solvate thereof, and optionally a pharmaceutically acceptable excipient:

(I)

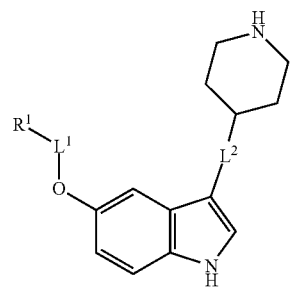

wherein:
L$^1$ is C$_{1-4}$ alkylene;
L$^2$ is C$_{2-4}$ alkylene;
R$^1$ is aryl or heteroaryl, wherein said aryl or said heteroaryl is optionally substituted with one or more groups independently selected from the group consisting of C$_{1-4}$ alkyl, halogen, —CF$_3$, —CN, —OH, —O(C$_{1-4}$ alkyl), —SH, —S(C$_{1-4}$ alkyl), —NH$_2$, —NH(C$_{1-4}$ alkyl), and —N(C$_{1-4}$ alkyl)(C$_{1-4}$ alkyl);
each R$^2$ is independently selected from the group consisting of C$_{1-4}$ alkyl, halogen, —CF$_3$, —CN, —OH, —O(C$_{1-4}$ alkyl), —SH, —S(C$_{1-4}$ alkyl), —NH$_2$, —NH(C$_{1-4}$ alkyl), and —N(C$_{1-4}$ alkyl)(C$_{1-4}$ alkyl);
R$^3$ is selected from the group consisting of hydrogen, C$_{1-4}$ alkyl, halogen, —CF$_3$, —CN, —OH, —O(C$_{1-4}$ alkyl), —SH, —S(C$_{1-4}$ alkyl), —NH$_2$, —NH(C$_{1-4}$ alkyl), and —N(C$_{1-4}$ alkyl)(C$_{1-4}$ alkyl);
R$^4$ is selected from the group consisting of hydrogen, C$_{1-4}$ alkyl, and —CO(C$_{1-4}$ alkyl);

R$^5$ is selected from the group consisting of hydrogen, C$_{1-4}$ alkyl, and —CO(C$_{1-4}$ alkyl); and
n is 0, 1, 2 or 3.

12. The pharmaceutical composition of claim 11, wherein said compound of formula (I) is a compound of formula (II)

(II)

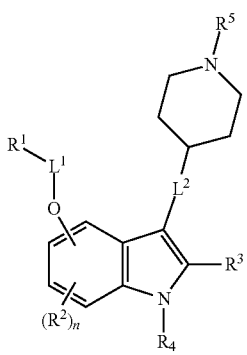

wherein:
L$^1$ is —(CH$_2$)$_{1-4}$—;
L$^2$ is —CH$_2$CH$_2$— or —CH$_2$CH$_2$CH$_2$—; and
R$^1$ is phenyl optionally substituted with one or more groups independently selected from the group consisting of C$_{1-4}$ alkyl, halogen, —CF$_3$, —CN, —OH, —O(C$_{1-4}$ alkyl), —SH, —S(C$_{1-4}$ alkyl), —NH$_2$, —NH(C$_{1-4}$ alkyl), and —N(C$_{1-4}$ alkyl)(C$_{1-4}$ alkyl);
or a pharmaceutically acceptable salt or solvate thereof.

13. A method of treating a gastrointestinal disease or disorder, the method comprising the administration of a therapeutically effective amount of a compound of formula (I) or a pharmaceutically acceptable salt or solvate thereof to a subject in need thereof:

(I)

wherein:
L$^1$ is C$_{1-4}$ alkylene;
L$^2$ is C$_{2-4}$ alkylene;
R$^1$ is aryl or heteroaryl, wherein said aryl or said heteroaryl is optionally substituted with one or more groups independently selected from the group consisting of C$_{1-4}$ alkyl, halogen, —CF$_3$, —CN, —OH, —O(C$_{1-4}$ alkyl), —SH, —S(C$_{1-4}$ alkyl), —NH$_2$, —NH(C$_{1-4}$ alkyl), and —N(C$_{1-4}$ alkyl)(C$_{1-4}$ alkyl);
each R$^2$ is independently selected from the group consisting of C$_{1-4}$ alkyl, halogen, —CF$_3$, —CN, —OH, —O(C$_{1-4}$ alkyl), —SH, —S(C$_{1-4}$ alkyl), —NH$_2$, —NH(C$_{1-4}$ alkyl), and —N(C$_{1-4}$ alkyl)(C$_{1-4}$ alkyl);
R$^3$ is selected from the group consisting of hydrogen, C$_{1-4}$ alkyl, halogen, —CF$_3$, —CN, —OH, —O(C$_{1-4}$ alkyl), —SH, —S($C_{1-4}$ alkyl), —$NH_2$, —NH($C_{1-4}$ alkyl), and —N($C_{1-4}$ alkyl)($C_{1-4}$ alkyl);

$R^4$ is selected from the group consisting of hydrogen, $C_{1-4}$ alkyl, and —CO($C_{1-4}$ alkyl);

$R^5$ is selected from the group consisting of hydrogen, $C_{1-4}$ alkyl, and —CO($C_{1-4}$ alkyl); and n is 0, 1, 2 or 3.

14. The method of claim 13, wherein said gastrointestinal disease or disorder is selected from the group consisting of constipation, dyspepsia and/or associated dyspeptic symptoms, irritable bowel syndrome, gastroparesis, intestinal pseudo-obstruction, obstructed defecation, abdominal bloating, abdominal distension, fecal impaction, and abdominal pain.

15. The method of claim 13, wherein the subject is a human.

16. A process of preparing a compound of formula (I-1) as defined in claim 1, the process comprising a step of reacting a compound of formula (Ib), either with hydrazine and a base or with lithium aluminum hydride, to obtain the compound of formula (I-1):

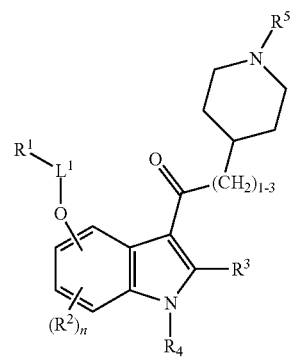

(Ib)

wherein $R^1$, $R^2$, $R^3$, $R^4$, $R^5$, $L^1$ and n in formula (Ib) have the same meanings as the corresponding groups or variables in the compound of formula (I-1).

* * * * *